United States Patent [19]

Carlson

[11] Patent Number: 4,713,772

[45] Date of Patent: Dec. 15, 1987

[54] AUTOMATIC ON-LINE CHEMISTRY MONITORING SYSTEM HAVING IMPROVED CALIBRATION UNIT

[75] Inventor: Gerald L. Carlson, Mt. Lebanon Township, Allegheny County, Pa.

[73] Assignee: Westinghouse Electric Corp., Pittsburgh, Pa.

[21] Appl. No.: 799,038

[22] Filed: Nov. 18, 1985

[51] Int. Cl.$^4$ .................. G06F 15/46; G01N 1/16
[52] U.S. Cl. .................. 364/496; 73/863.31;
  73/864.81; 137/625.11; 364/509; 364/556;
  364/571; 422/62
[58] Field of Search ............ 364/496, 497, 500, 571,
  364/556; 73/836.01, 863.31, 863.33, 864.81, 1
  R; 422/62; 137/564.5, 552.5, 607, 625.11

[56] References Cited

U.S. PATENT DOCUMENTS

| | | | |
|---|---|---|---|
| 2,865,388 | 12/1958 | Sternbergh | 137/564.5 |
| 3,025,876 | 3/1962 | Wolfe | 137/564.5 |
| 3,095,892 | 7/1963 | Laing et al. | 137/564.5 |
| 3,720,230 | 3/1973 | Stockstill | 137/564.5 |
| 3,800,288 | 3/1974 | Russell et al. | 364/200 |
| 3,928,197 | 12/1975 | Horan, Jr. et al. | 210/101 |
| 4,151,255 | 4/1979 | Capuano et al. | 324/438 |
| 4,204,259 | 5/1980 | Yabe | 364/497 |
| 4,204,430 | 5/1980 | Tamm et al. | 73/1 R |
| 4,221,567 | 9/1980 | Clark et al. | 73/1 R |
| 4,275,448 | 6/1981 | Le Dall | 364/500 |
| 4,341,124 | 7/1982 | Rodgers et al. | 73/863.01 |
| 4,357,300 | 11/1982 | Nicklaus et al. | 364/497 |
| 4,414,858 | 11/1983 | Peterson et al. | 73/863.33 |
| 4,472,354 | 9/1984 | Passell et al. | 422/62 |
| 4,482,967 | 11/1984 | Evans, Jr. et al. | 364/496 |
| 4,490,236 | 12/1984 | Petty | 73/1 R |
| 4,568,465 | 2/1986 | Davis et al. | 364/500 |
| 4,628,748 | 12/1986 | Jogan et al. | 73/863.01 |

FOREIGN PATENT DOCUMENTS

2462281 9/1976 Fed. Rep. of Germany .
2482306 11/1981 France .
915791 1/1963 United Kingdom .

Primary Examiner—Errol A. Krass
Assistant Examiner—Kevin J. Teska

[57] ABSTRACT

A system for automatically sampling, monitoring and analyzing power plant steam cycle water supplied from various points in a power plant steam cycle system as a plurality of influent fluid sample streams. Plural continuous monitor modules each include continuous on-line monitors and provide continuous on-line monitoring of a corresponding influent fluid sample stream, and an ion chromatograph unit provides semi-continuous monitoring of a selected one of the influent fluid sample streams. Each continuous monitor module also includes an improved calibration unit including a conditioning unit which creates a pressure differential in the influent fluid sample stream and utilizes the pressure differential to inject a mixed standard solution into the influent fluid sample stream, thereby providing a conditioned influent fluid sample stream having predetermined chemical characteristics; the continuous on-line monitors are calibrated with respect to the predetermined chemical characteristics of the corresponding conditioned influent fluid sample stream and the ion chromatograph unit is calibrated with respect to the predetermined chemical characteristics of the selected conditioned influent fluid sample stream supplied thereto. A control unit receives signals representative of the monitored chemical characteristics from the continuous on-line monitors and the ion chromatograph unit and uses these signals in a feedback loop to control the monitoring system, to automatically calibrate the continuous on-line monitors and the ion chromatograph unit in accordance with the predetermined chemical characteristics of the conditioned influent fluid sample streams, and to detect, analyze and correct steam cycle water chemistry changes before corrosion or other problems related to water chemistry imbalances.

12 Claims, 17 Drawing Figures

AUTOMATIC ON-LINE CHEMISTRY MONITORING SYSTEM HAVING IMPROVED CALIBRATION UNIT

CROSS REFERENCES TO RELATED APPLICATIONS

The present application is related to copending patent application Ser. No. 793,061, filed Oct. 30, 1985, for AUTOMATIC ON-LINE CHEMISTRY MONITORING SYSTEM, by Byers, Carlson, Wooten, Richards and Pensenstadler, assigned to the assignee of the present application, and co-pending patent application Ser. No. 782,858, filed Oct. 2, 1985, for ON-LINE CALIBRATION SYSTEM FOR CHEMICAL MONITORS, also assigned to the assignee of the present application.

BACKGROUND OF THE INVENTION

1. Field of the Invention

The present invention generally relates to a system for automatically sampling, monitoring and analyzing power plant steam cycle water from a plurality of points in a power plant steam system and, more particularly, to a system for performing continuous on-line chemical monitoring using continuous on-line monitors, and semi-continuous on-line monitoring using an ion chromotograph unit, for controlling the monitoring with real-time feedback from the continuous on-line monitors and the ion chromatograph unit, for automatically analyzing the monitored chemical characteristics, and for automatically calibrating the continuous on-line monitors and the ion chromatograph unit with an improved autocalibration unit.

2. Description of the Related Art

The control of impurities in power plant steam cycle water is recognized as being essential to the protection of a power plant's steam system against corrosion related failures. In spite of advances in methods for detecting and measuring impurities, or contaminants, at ultra-trace concentration levels, plant chemistry monitoring is, for the most part, based on the on-line monitoring of only a few chemical characteristics, such as conductivity, pH, and dissolved oxygen concentration. Many critical impurities which cause corrosion, such as chloride and sulfate, are checked only once or twice a day by laboratory analysis of grab samples. Grab sample data, since obtained only at long intervals, provides only an historical record of plant chemistry and is of little use in controlling the levels of corrosion causing impurities and thus in the prevention of corrosion related failures. Furthermore, on-line monitor information which is available, is provided only as strip chart records which require tedious operator analysis.

In current instrumentation, particularly cation conductivity monitors, the composition of the fluid sample, or solution, to be monitored is assumed at the time that the instrument is manufactured. The calculation of temperature compensated cation conductivity values, however, is dependent on the measured cation conductivity and solution composition. Thus, temperature compensated cation conductivity values will be erroneous if the actual solution composition differs from the assumed composition. The lack of real time feedback in prior monitoring systems prevents accurate temperature compensation since the actual solution composition cannot be factored into the temperature compensation.

Current monitoring systems also suffer from a lack of integrated calibration capability. Calibration is usually a scheduled maintenance operation; thus, calibration problems or equipment failures which occur between scheduled calibrations could go undetected and uncorrected until the next scheduled calibration. Moreover, as a scheduled maintenance operation, calibration has usually been performed manually as an off-line procedure using standards which may be significantly different than the sample, for example, highly concentrated buffer solutions.

Several systems have been developed to monitor power plant steam cycle water. U.S. Pat. No. 4,414,858, Peterson et al., assigned to the Assignee of the present application, discloses a system for sampling fluids with a plurality of fluid sample lines connected to various points in a power plant steam system. A valve arrangement connects a selected fluid sample line to an analyzer, and passes the non-selected fluid samples to a common drain line which is connected back to the power plant steam system. A microprocessor controls the valve arrangement in accordance with a set of stored instructions to selectively connect each of the sample fluid lines to the analyzer in a sampling sequence, and controls the analyzer with open loop control. Each fluid sample line also includes a sensor which provides an output signal to the microprocessor, which alters the sampling sequence if a particular sensor output indicates an alarm condition. This system provides only one on-line monitor per sample stream, and thus monitors one chemical characteristic of each sample fluid stream. Further, calibration of the sensors and the analyzer is performed manually in an off-line procedure.

Another system for monitoring steam producing water is disclosed in U.S. Pat. No. 4,472,354, Passell et al. This system uses ion chromatographic analysis to provide an ion profile of the steam producing water. Plural sampling systems collect the steam producing water supplied from a multiple number of points in a power plant steam system over a five to six-hour time period, called a fill cycle. At the end of the fill cycle, the water collected in a particular sampling system is supplied to the ion chromatographs. Thus, the system does not provide for continuous on-line monitoring of the steam producing water at each point in the plant steam/water cycle, but rather a periodic monitoring of a fluid sample collected over a five to six hour period to provide an ion profile of the steam producing water flowing in the plant. This system does not employ any continuous on-line monitors, and uses open loop control of the operation of the ion chromatographs. In this system, calibration is performed by diluting a standard solution with pure water and providing the diluted solution directly to the ion chromatographs in response to an operator decision.

SUMMARY OF THE INVENTION

In accordance with the present invention, there is provided a system for automatic continuous on-line monitoring of the water chemistry of each of a plurality of influent fluid sample streams from various points in a power plant steam system. The monitoring system of the present invention combines analytical instruments and monitors with computerized control and data logging. More particularly, a plurality of continuous monitor modules each include continuous on-line monitors for continuous on-line monitoring of a respective one of the influent fluid sample streams and and an improved calibration unit for selectively producing a conditioned influent fluid sample stream having predetermined chemical characteristics against which the continuous on-line monitors may be calibrated, and an ion chromatograph unit provides semi-continuous monitoring of species for which no simple on-line monitor is available in a selected one of the influent fluid sample streams. The ion chromatograph unit may be calibrated with respect to the predetermined chemical chracteristics of one of the conditioned influent fluid sample streams.

In accordance with the present invention, an improved calibration unit includes a conditioning unit which creates a pressure differential in the influent fluid sample stream and utilizes the pressure differential to inject a mixed standard solution into the influent fluid sample stream, thereby providing the conditioned influent fluid sample stream. The use of fluid dynamics, the pressure differential, provides a self-regulating unit that maintains a precise ratio of mixed standard solution to the influent fluid sample stream regardless of the flow rate or temperature of the influent fluid sample stream. This improved calibration unit also eliminates the need for a pump to inject the mixed standard solution, pumps being subject to drift in the adjustment of the injection rate, subject to mechanical failure, and costly. Further, the conditioning unit requires no electricity and has no moving parts. Conditioning of the influent fluid sample streams is easily automated and provides for on-line calibration. Moreover, the use of a conditioned influent fluid sample stream allows the continuous on-line monitors and the ion chromatograph unit to be calibrated in the range in which monitoring is performed, rather than a range dictated by a convenient standard or a highly concentrated buffer solution.

The monitoring system is controlled by a control unit including a microcomputer or a minicomputer. The control unit receives signals representative of the monitored chemical characteristics from the continuous on-line monitors and the ion chromatograph unit, and uses these signals in a feedback loop to detect monitor failures, to determine the sequence in which the plural influent fluid sample streams are supplied to the ion chromatograph unit, to control operation of the ion chromatograph unit, and to automatically calibrate the contnuous on-line monitors and the ion chromatograph unit. The control unit also logs data from the continuous monitor modules and the ion chromatograph unit, and interfaces with a plant data center. Thus, steam cycle water chemistry changes can be detected, diagnosed, and corrected before corrosion or other problems related to water chemistry imbalances can occur.

In the monitoring system of the present invention each continuous monitor module monitors the temperature of and performs preliminary processing of the corresponding influent fluid sample stream. The preliminary processing includes, for example providing the influent fluid sample stream with a predetermined volumetric flow rate, deionizing the influent fluid sample stream, and the above-mentioned conditioning to perform calibration. Then, the continuous monitor module divides each influent fluid sample stream into first and second influent fluid sample streams. The continuous on-line monitors, in the continuous monitor module, monitors selected chemical characteristics of the first influent fluid sample stream, and temperature and continuous monitor signals, representative of the monitored temperature and chemical characteristics, are generated. The second influent fluid sample streams provided by the continuous monitor modules are further divided into third and fourth influent fluid sample streams and a plurality of cation conductivity monitors monitor the cation conductivity of each of the third influent fluid sample streams and generate cation conductivity signals representative of the monitored cation conductivity. Further, each cation conductivity monitor provides an altered, third fluid sample stream from which cations have been removed. Each of the plural, altered third and the corresponding fourth influent fluid sample streams are selectively supplied to the ion chromatograph unit in individual succession, in accordance with a predetermined sampling sequence. The ion chromatograph unit performs chromatographic monitoring of selected chemical characteristics, in accordance with chromatograph actuation signals, and generates chromatograph signals representative of the monitored chemical characteristics. The control unit receives the temperature, continuous monitor, cation conductivity, and chromatograph signals, determines the sampling sequence and interrupts the sampling sequence in response to an abnormal one of the output signals, stores predetermined conductivity equations and data, and performs a variety of analytical functions to control the operation of the monitoring system with a feedback loop. The functions performed by the control unit include, for example: calculating a strong acid temperature compensated cation conductivity in accordance with predetermined conductivity equations, the monitored temperature, and the chemical characteristics monitored by the ion chromatograph unit; comparing the strong acid temperature compensated cation conductivity with the monitored cation conductivity to select the chemical characteristics to be monitored by the ion chromatograph unit; generating the chromatograph actuation signals in accordance with the chemical characteristics selected by comparing the temperature compensated cation conductivity with the monitored cation conductivity; calculating a cation conductivity including organic acids at the monitored temperature; comparing the monitored temperature cation conductivity including organic acids with the monitored cation conductivity to determine if calibration is required; selectively generating the calibration actuation signals at predetermined time intervals and between the predetermined time intervals; and calibrating the continuous monitor, cation conductivity and chromatograph signals with respect to the predetermined chemical characteristics of the conditioned influent fluid sample stream.

One embodiment of a continuous monitor module comprises a continuous monitor unit including continuous on-line monitors for monitoring chemical characteristics selected from the group of sodium, dissolved oxygen, hydrazine, ammonia, pH, and specific conductivity.

One embodiment of the ion chromatograph unit comprises an anion chromatograph for monitoring anions, an organic acid chromatograph for monitoring organic acids, and a cation chromatograph for monitoring cations, each of said anion, organic acid and cation chromatographs having a sample volume control unit for preparing a sample volume of an influent fluid sample stream for monitoring in accordance with corresponding anion, organic acid, and cation chromatograph sample volume control unit actuation signals. For this embodiment of the ion chromatograph unit, the control unit calculates a sample volume of the altered, third fluid sample stream to be prepared for monitoring by the anion and organic acid chromatograph sample volume control units in accordance with the monitored cation conductivity of the altered, third fluid sample stream being supplied to the ion chromatograph means and generates the anion and organic acid chromatograph sample volume actuation signals based on the calculated sample volume of the third influent fluid sample stream, and calculates a sample volume of the fourth influent fluid sample stream to be prepared for monitoring by the cation chromatograph sample volume control unit in accordance with the monitored specific conductivity of the fourth influent fluid sample stream being supplied to the ion chromatograph unit and generates the cation chromatograph actuation signals based on the calculated sample volume of the fourth influent fluid sample stream.

DESCRIPTION OF THE PREFERRED EMBODIMENTS

Figure 1:
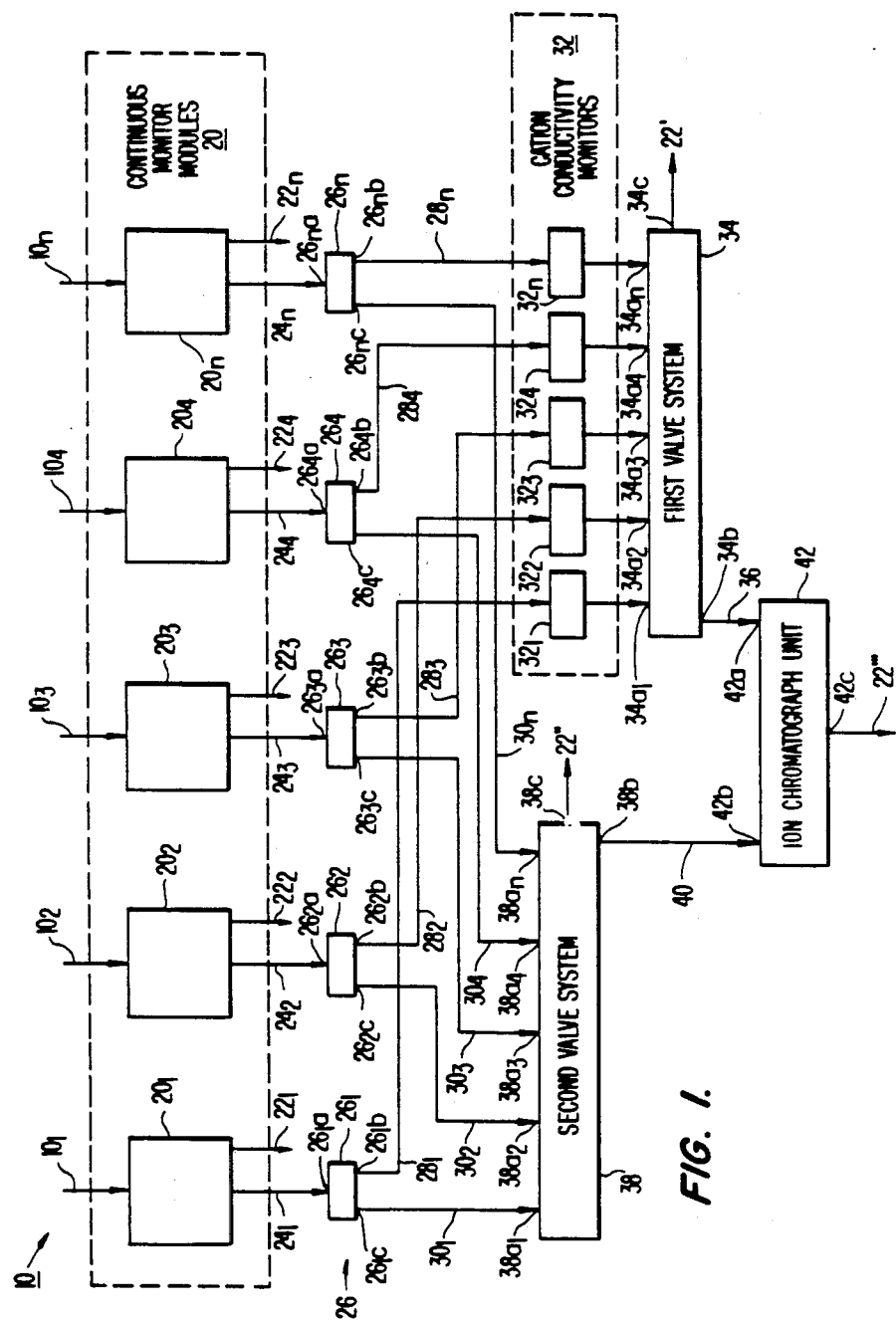
FIG. 1 is a block diagram of the monitoring system of the present invention.

The block diagram of FIG. 1 illustrates the overall monitoring system of the present invention. Fluid lines 10, individually designated $10_1$, $10_2$ ... $10_n$, supply plural influent fluid sample streams of steam cycle water from a plurality of different points in a power plant steam system to respective ones of a plurality of continuous monitor modules 20, individually designated $20_1$, $20_2$ ... $20_n$. It is to be understood that the system of the present invention may be used in any type of steam generating electrical power plant, whether fossil or nuclear fueled, and may accommodate any number of sample lines, as is deemed desirable. Each continuous monitor module 20 performs preliminary processing (described below) of the corresponding influent fluid sample stream and then divides the corresponding influent fluid sample stream received thereby into first and second influent fluid sample streams; the module 20 then analyzes the first influent fluid sample stream and thereafter directs same to a drain 22. Further, each of the modules 20 supplies a second influent fluid sample stream through a second fluid line 24 to the input 26a of a corresponding one of a plurality of second influent fluid sample stream flow-splitters 26, individually designated $26_1$, $26_2$ ... $26_n$, which divides same into third and fourth influent fluid sample streams (or fractional portions) at its outputs 26b and 26c, respectively. Corresponding ones of a plurality of third fluid lines 28 and fourth fluid lines 30 are respectively connected to the first and second outputs 26b and 26c of the second influent fluid sample stream flow-splitters 26. Cation conductivity monitors 32 are provided in each third fluid line 28 to monitor the cation conductivity of the third influent fluid sample streams and to generate cation conductivity signals representative of the monitored cation conductivities; the cation conductivity monitors 32 also remove cations from the third influent fluid sample stream to produce an altered third fluid sample stream.

A first valve system 34 receives the altered third influent fluid sample streams from the cation conductivity monitors 32 at corresponding ones of a plurality of inputs 34a, and selectively supplies one of the altered third fluid sample streams to a first output 34b thereof and the remaining altered third fluid sample streams to the second output 34c thereof. A first valve system output line 36 is connected to the first output 34b and a drain 22' is connected to a second output 34c. A second valve system 38 receives the fourth influent fluid sample streams from the second outputs 26c of the second influent fluid sample stream flow splitters 26 at corresponding ones of a plurality of inputs 38a via the fourth fluid lines 30, and selectively supplies one of the fourth influent fluid sample streams to a first output 38b thereof and the remaining fourth influent fluid sample streams to a second output 38c thereof. A second valve system output line 40 is connected to the first output 38b and a drain 22" is connected to the second output 38c. The first and second valve systems 34, 38 operate to supply one of each of the altered third and fourth influent fluid sample streams at first outputs 34b, 38b, respectively, in individual succession, in accordance with a predetermined sampling sequence and with first and second valve system actuation signals. One example of a sampling system for use as the first and second valve systems 34, 38 is disclosed in U.S. Pat. No. 4,414,858, Peterson et al., assigned to the Assignee of the present invention, the disclosure of which is hereby incorporated by reference.

An ion chromatograph unit 42 receives the selected ones of the altered third and fourth influent fluid sample streams supplied by the first and second valve sytems 34, 38 at respective first and second inputs 42a, 42b through the first and second valve system output lines 36, 40. An output 42c of the ion chromatograph unit 42 is connected to a drain 22'''.

Figure 2:
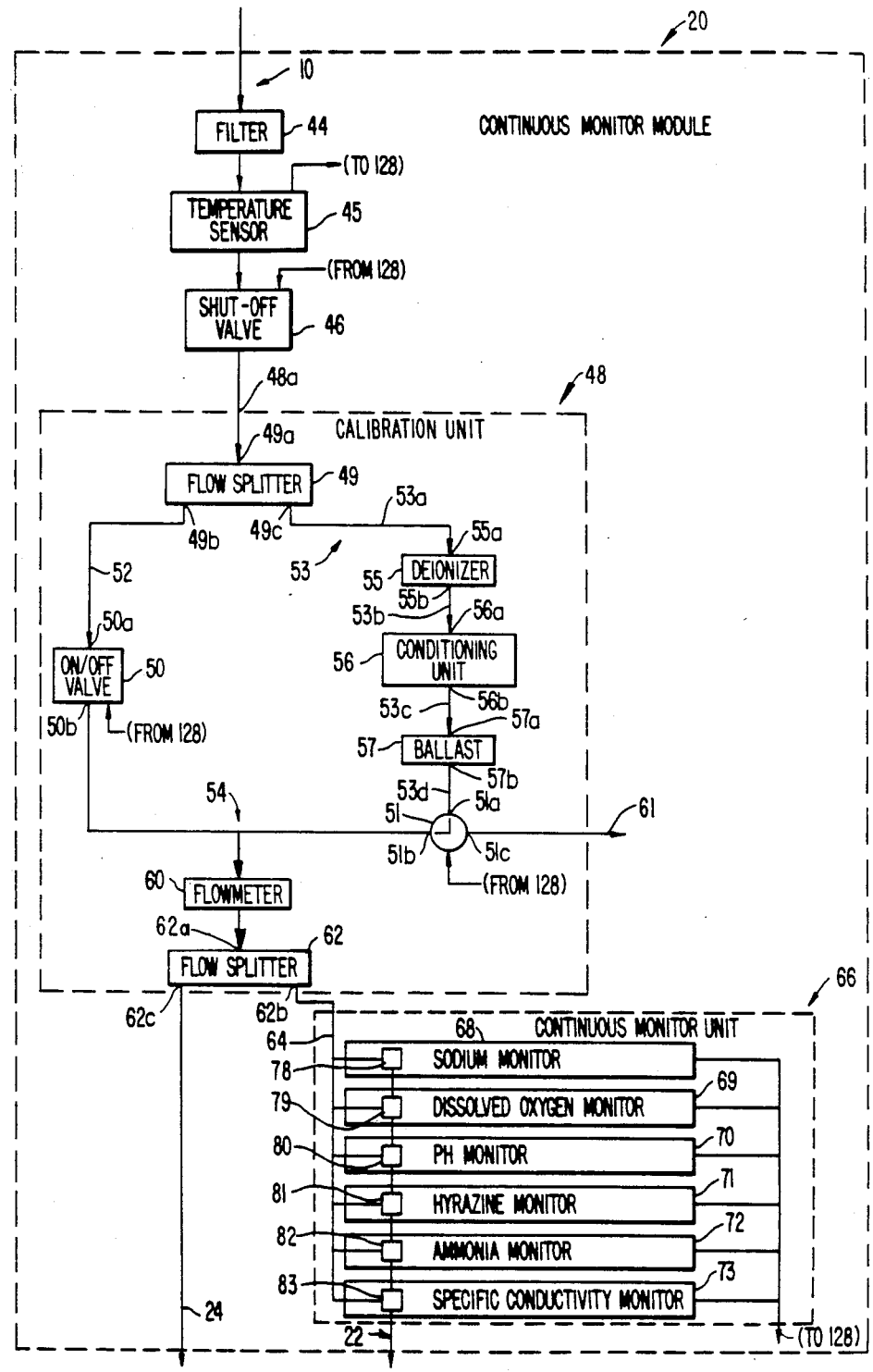
FIG. 2 is a block diagram of one embodiment of a continuous monitor module of the monitoring system.

An example of one continuous monitor module 20 is shown in the block diagram of FIG. 2. The influent fluid sample stream supplied by the fluid line 10 flows through a filter 44, a temperature sensor 45, and a shut off valve 46, the temperature sensor 45 sensing the temperature of the influent fluid sample stream and generating a temperature signal representative of the sensed temperature. The influent fluid sample stream then flows to a calibration unit 48, entering the calibration unit 48 at an input 48a thereof. The calibration unit 48 includes a flow-splitter 49 for receiving the influent fluid sample stream at its input 49a and for providing first and second portions of the influent fluid sample stream and its first and second outputs 49b and 49c, respectively. An on-off valve 50 and a two-way valve 51, together with a first parallel fluid line 52, a second parallel fluid line 53 and an output fluid line 54, are selectively operable to establish a first fluid sample stream flow path for providing the first portion of the influent fluid sample stream to an output 48b of the calibration unit, a second fluid sample stream flow path for providing the second portion of the influent fluid sample stream to a deionizer 55, a conditioning unit 56, and a ballast 57, thereby providing a conditioned, deionized influent fluid sample stream to a flowmeter 60 and a third fluid sample stream flow path for providing the conditioned, deionized fluid sample stream to a drain 61. The deionizer 55 is a standard mixed bed deionizer for providing a deionized influent fluid sample stream, and the conditioning unit 56 (described below in detail with reference to FIG. 6) creates a pressure differential in the influent fluid sample stream and utilizes the pressure differential to inject a mixed standard solution into the deionized influent fluid sample stream, thereby providing a conditioned, deionized influent fluid sample stream (hereinafter the "conditioned influent fluid sample stream") having predetermined chemical characteristics. The ballast 57 ensures that the chemical charcteristics of the conditioned influent fluid sample stream are stable.

The on-off valve 50 has an input 50a and an output 50b, the input 50a being interconnected with the first output 49b of the flow-splitter 49 by the first parallel fluid line 52, and the output 50b being interconnected with the output 48b of the calibration unit 48 by the output fluid line 54. The on-off valve 50 is selectively operable to establish open and closed positions; the on-off valve 50, in the open position thereof, interconnecting the first paralle fluid line 52 and the output fluid line 54 to establish the first fluid sample stream flow path. The two-way valve 51 has an input 51a, a first output 51b, and a second output 51c, and is selectively operable between first and second positions, the first position connecting the input 51a and the first output 51b thereof, and the second position connecting the input 51a and the second output 51c thereof. The second parallel fluid line 53 has a first portion 53a which interconnects the second output 49c of the flow-splitter 49 and an input 55a of the deionizer 55, a second portion 53b which interconnects an output 55b of the deionizer 55 and an input 56a of the conditioning unit 56, a third portion 53c which interconnects an output 56b of the conditioning unit 56 and an input 57a of the ballast 57, and a fourth portion 53d which interconnects an output 57b of the ballast 57 with the input 51a of the two-way valve 51. The two-way valve, in the first position thereof, interconnects the second parallel fluid line 53 with the output fluid line 54 and establishes therewith, and with the deionizer 55, the conditioning unit 56, and the ballast 57, the second fluid sample stream flow path. The two-way valve, in the second position thereof, interconnects the second parallel fluid line 53 with the drain 61 and establishes therewith, and with the deionizer 55, the conditioning unit 56, and the ballast 57, the third fluid sample stream flow path.

The calibration unit 48 further includes an influent fluid sample stream flow-splitter 62 for dividing the influent fluid sample stream into first and second influent fluid sample streams at its first and second outputs 62b, 62c, respectively. A first fluid line 64 is connected to the first output 62b of the influent fluid sample stream flow-splitter 62 and the second fluid sample line 24 is connected to the second output 62c of the influent fluid sample stream flow-splitter 62. The calibration unit 48 and the filter 44 perform the previously mentioned preliminary processing.

The preferrred embodiment of the calibration unit 48 includes the deionizer 55 and the ballast 57; however it is possible to eliminate the deionizer 55 so that the influent fluid sample stream, rather than a deionized influent fluid sample stream, is conditioned, and to eliminate the ballast if the conditioning unit provides a conditioned influent fluid sample stream having uniform and stable chemical characteristics. Alternative embodiments of valve system arrangements for establishing various flow paths in the calibration unit so as to selectively provide, as outputs thereof, the influent fluid sample stream and a conditioned influent fluid sample stream are disclosed in patent application Ser. No. 782,858.

Each continuous monitor module 20 further comprises a continuous monitor unit 66 for continuous on-line monitoring of the first influent fluid sample stream The continuous monitor unit 66 in each continuous monitor module 20 contains as many chemical monitors, connected in parallel by the first fluid line 64, as necessary to analyze the chemical characteristics of a specific influent fluid sample stream—the chemical characteristics of each influent fluid sample stream being dependent on the particular point in the power plant steam cycle from which the influent fluid sample stream is taken. Thus, each continuous monitor unit 66 includes various continuous on-line monitors, including, for example, a sodium monitor 68, a dissolved oxygen monitor 69, a pH monitor 70, a hydrazine monitor 71 an ammonia monitor 72, and a specific conductivity monitor 73. The various monitors 68–73 comprise corresponding detectors, e.g., sodium detector 78, dissolved oxygen detector 79, pH detector 80, hydrazine detector 81, ammonia detector 82, and specific conductivity detector 83, and each detector 78–83 comprises a flow cell (not shown) and a sensor (not shown) provided in the flow cell for monitoring the level of the corresponding chemical chracteristic of a fluid sample stream. Each monitor produces an output representative of the monitored level of the corresponding chemical characteristic, the output being, for example, a visual display or an electrical signal. The continuous on-line monitors 68–73 may be standard monitors produced by Martek, Orion, Orbisphere, or Leeds & Northrup, for example.

To calibrate the monitors 68–73 in the continuous monitor unit 66, the calibration unit 48 establishes the second fluid sample stream flow path to provide the conditioned, deionized influent fluid sample stream which has known concentrations of selected chemicals and thus predetermined chemical characteristics, to the output 48b of the calibration unit 48. The second fluid sample stream flow path is established in accordance with calibration actuation signals for operating the on-off valve 50 to establish the closed position thereof and the two-way valve 51 to establish the first position thereof.

When calibration is not being performed, the calibration unit 48 establishes the first and third fluid sample stream flowpaths to provide the first portion of the influent fluid sample stream to the output 48b of the calibration unit for monitoring and to provide the second portion of the influent fluid sample stream to the conditioning unit 56 and then to the drain 61. It is desirable to maintain a continuous flow through the conditioning unit so that the chemical characteristics of the conditioned influent fluid sample stream are stabilized, thereby permitting calibration to be performed without waiting for the chemical characterisics of the conditioned influent fluid sample stream to stabilize. If a continuous flow is not maintained, an excess of the mixed standard solution may accumulate in a portion of the influent fluid sample stream, thereby disturbing the predetermined chemical characteristics of the conditioned influent fluid sample stream.

The conditioned influent fluid sample stream is divided into first and second conditioned influent fluid sample streams by the influent fluid sample stream flow-splitter 62 and the conditioned first fluid sample stream is supplied to each of the monitors 68–73 by the first fluid line 64. The output of each of the monitors 68–73 is calibrated with respect to the predetermined chemical characteristics of the conditioned first influent fluid sample stream, as is known in the art, by a control unit which is described later. Further, the conditioned second influent fluid sample stream provided by one of the continuous monitor modules 20 can be used to calibrate the ion chromatograph unit 42. By using a flowing conditioned influent fluid sample stream, rather than a stagnant buffer solution, to calibrate the monitors 68–73, the monitoring system of the present invention calibrates the detectors 78–83 in the same environment in which they monitor the chemical characteristics of the influent fluid sample stream. An on-line calibration system for chemical monitors is disclosed in a copending U.S. patent application Ser. No. 782,858, assigned to the Assignee of the present invention.

Figure 3:
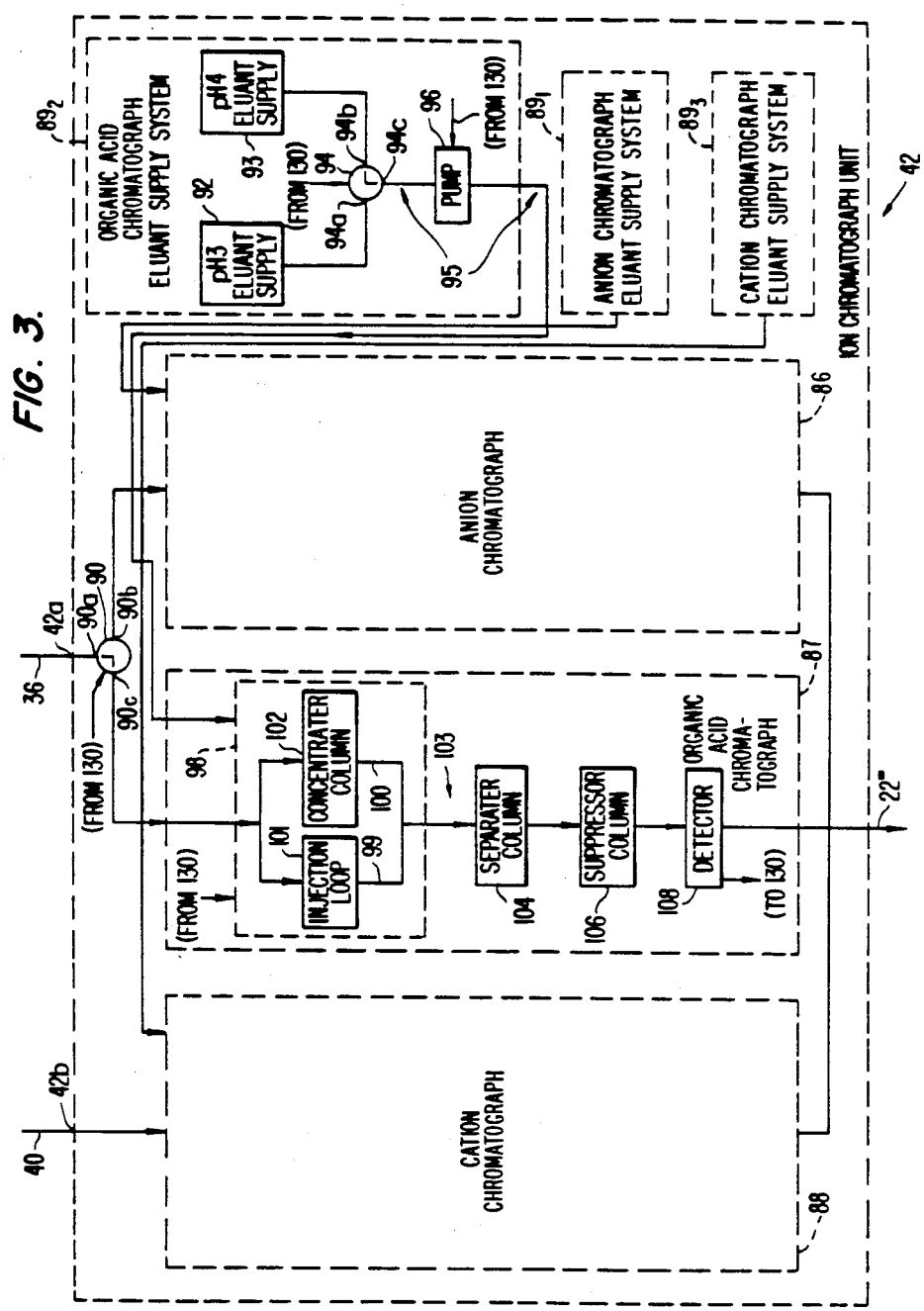
FIG. 3 is a simplified block diagram of portions of an ion chromatograph unit.

The ion chromatograph unit 42 is illustrated in the simplified block diagram of FIG. 3. One example of the ion chromatograph unit 42 contemplated for use in the monitoring system of the present invention is a Dionex Model 8000 ion chromatograph. The ion chromatograph unit 42 comprises, for example, an anion chromatograph 86, an organic acid chromatograph 87, a cation chromatograph 88, an anion chromatograph eluant supply system $89_1$ an organic acid chromatograph eluant supply system $89_2$, and a cation chromatograph eluant supply system $89_3$. A chromatograph selector valve 90 has an input 90a for receiving one of the altered third fluid sample streams from the first input 42a of the ion chromatograph unit 42 and first and second outputs 90b and 90c in fluid communication with the anion chromatograph 86 and the organic acid chromatograph 87, respectively. A chromatograph selector valve actuation signal operates the chromatograph selector valve 90 between first and second positions, the first position connecting the input 90a and the first output 90b thereof, and the second position connecting the input 90a and the second output 90c thereof. The chromatograph selector valve 90 is ordinarily in the first position to provide the altered third fluid sample stream to the anion chromatograph 86, and is selectively actuated to connect the input 42a with the organic acid chromatograph 87 only when it is determined that organic acid analysis is required, as described below. Organic acid chromatography is performed only when necessary since the suppressor column in the organic acid chromatograph 87 must be replaced relatively often, at a high cost. The cation chromatograph 88 receives one of the fourth fluid sample streams from the second input 42b of the ion chromatograph unit 42.

The anion, organic acid and cation chromatographs 86–88, and the anion, organic acid and cation chromatograph eluant supply systems $89_1$–$89_3$ include substantially similar, corresponding elements, and thus only the organic acid chromatograph 87 and the organic acid chromatograph eluant supply system $89_2$ are illustrated and described in detail.

The organic acid chromatograph eluant supply system $89_2$ comprises plural eluant supplies, for example, a pH 3 eluant supply 92 and a pH 4 eluant supply 93 for storing and supplying pH 3 and pH 4 eluants, respectively. An eluant selector valve 94 has first and second inputs 94a, 94b in fluid communication with respective ones of the eluant supplies 92, 93, and is actuable, in accordance with an eluant selector valve actuation signal, to provide a selected one of the eluants to its output 94c. An eluant supply line 95 connects an eluant pump 96 to receive the output of the eluant selector valve 94. The eluant pump 96 supplies the selected eluant to each of the chromatographs 86–88 at a predetermined volumetric rate via the eluant supply line 95, in accordance with an eluant volume actuation signal.

Whereas the organic acid chromatograph eluant supply system $89_2$ supplies plural eluants, the anion and cation chromatograph eluant supply systems $89_1$, $89_3$ only provide a single eluant; thus, the anion and cation chromatograph eluant supply systems $89_1$, $89_3$ do not require a selector valve. The eluant supplied to the anion chromatograph 86 is a mixture of carbonate and bicarbonate and the eluant supplied to the cation chromatograph 88 is hydrochloric acid HCl or nitric acid $HNO_3$.

The organic acid chromatograph unit 87 comprises a sample volume control unit 98 which prepares a sample volume of the altered third fluid sample stream being supplied to the first input 42a of the ion chromatograph unit 42 for analysis by the organic acid chromatograph 87. The sample volume control unit 98 basically includes first and second parallel fluid lines 99, 100, an injection loop 101 and a concentrator column 102. Further details of the sample volume control unit 98 are illustrated in and explained with respect to FIG. 5. The organic acid chromatograph unit 87 also comprises a chromatograph fluid line 103, which connects a separator column 104, a suppressor column 106 and a detector 108 in a fluid series circuit.

An example of the strength of the integrated monitoring system of the present invention is the placement of the cation conductivity monitors 32 ahead of, or upstream from, the ion chromatograph unit 42. Ammonia, which is present at relatively high concentrations in most power plant steam cycle water, causes problems in the detection of anions by the anion chromatograph 86. By supplying the third influent fluid sample streams to the cation conductivity montiors 32, which remove cations including ammonia from a fluid sample to provide the altered third fluid sample stream, prior to supplying one of the third influent fluid sample streams to the anion chromatograph 86, ammonia is removed from the third influent fluid sample stream before it is supplied to the anion chromatograph 86, thereby eliminating this serious problem.

Figure 4:
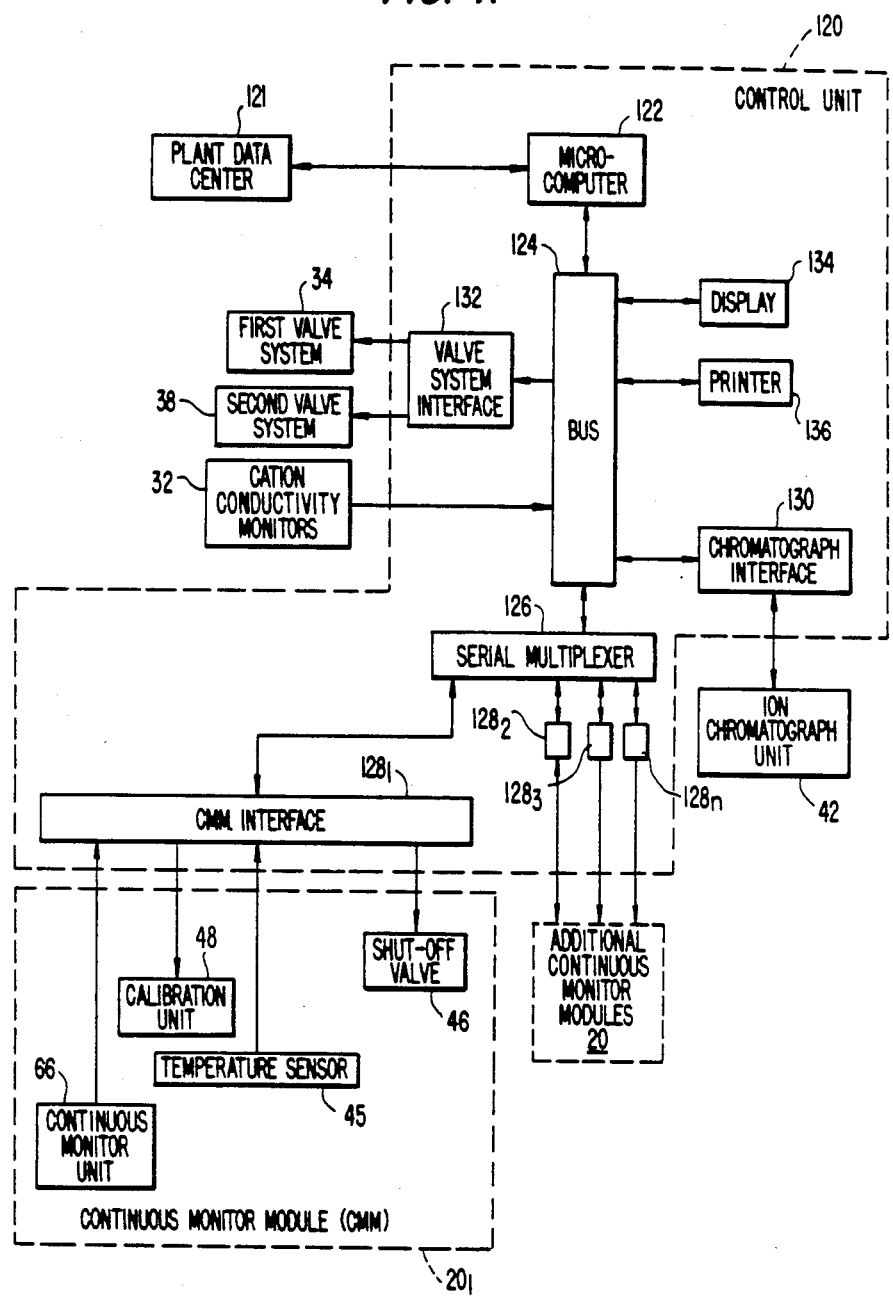
FIG. 4 is a schematic diagram of the monitoring system of the present invention.

FIG. 4 is a schematic diagram illustrating a control unit 120 which interfaces with the continuous monitor modules 20, the cation conductivity monitors 32, the first and second valve systems 34, 38, and the ion chromatograph unit 42, as well as a power plant data center 121, to provide fully automatic water chemistry monitoring and calibration functions and to interface with overall plant operation. The control unit 120 includes a microcomputer 122, a data bus 124, a serial multiplexer 126, a plurality of continuous monitor module (CMM) interfaces 128, individually designated $128_1$, $128_2$, ... $128_n$, corresponding to respective ones of the continuous monitor modules 20, a chomatograph interface 130, a valve system interface 132, a display 134, and a printer 136. The bus 124 receives control signals generated by the microcomputer 122 and supplies the control signals to the valve system interface 132, the CMM interfaces 128 via the serial multiplexer 126, and the chromatograph interface 130. Each CMM interface 128 may be, for example, Martek interface module, Model Mark XX, for receiving the temperature signals from temperature sensor 45 and the continuous monitor signals from continuous monitor unit 66, and providing actuator signals to shutoff valve 46 and the calibration unit 48.

The control signals generated by the microcomputer 122 include calibration control signals, eluant supply control signals, sample volume control unit control signals for each of the chromatographs 86–88, chromatograph selector means control signals and first and second valve system control signals. These control signals are converted to corresponding actuator signals by the CMM interfaces 128, the chromatograph interface 130 and the valve system interface 132, each of which functions as a decoder/driver to generate the actuator signals necessary to operate the various valves and pumps at the appropriate voltages. The bus 124 also receives the chromatograph signals via th chromatograph interface 130 and the temperature signals and the continuous monitor signals generated by each continuous monitor module 20 via corresonding CMM interfaces 128 and the serial multiplexer 126 and supplies these signals to the microcomputer 122.

Figure 5:
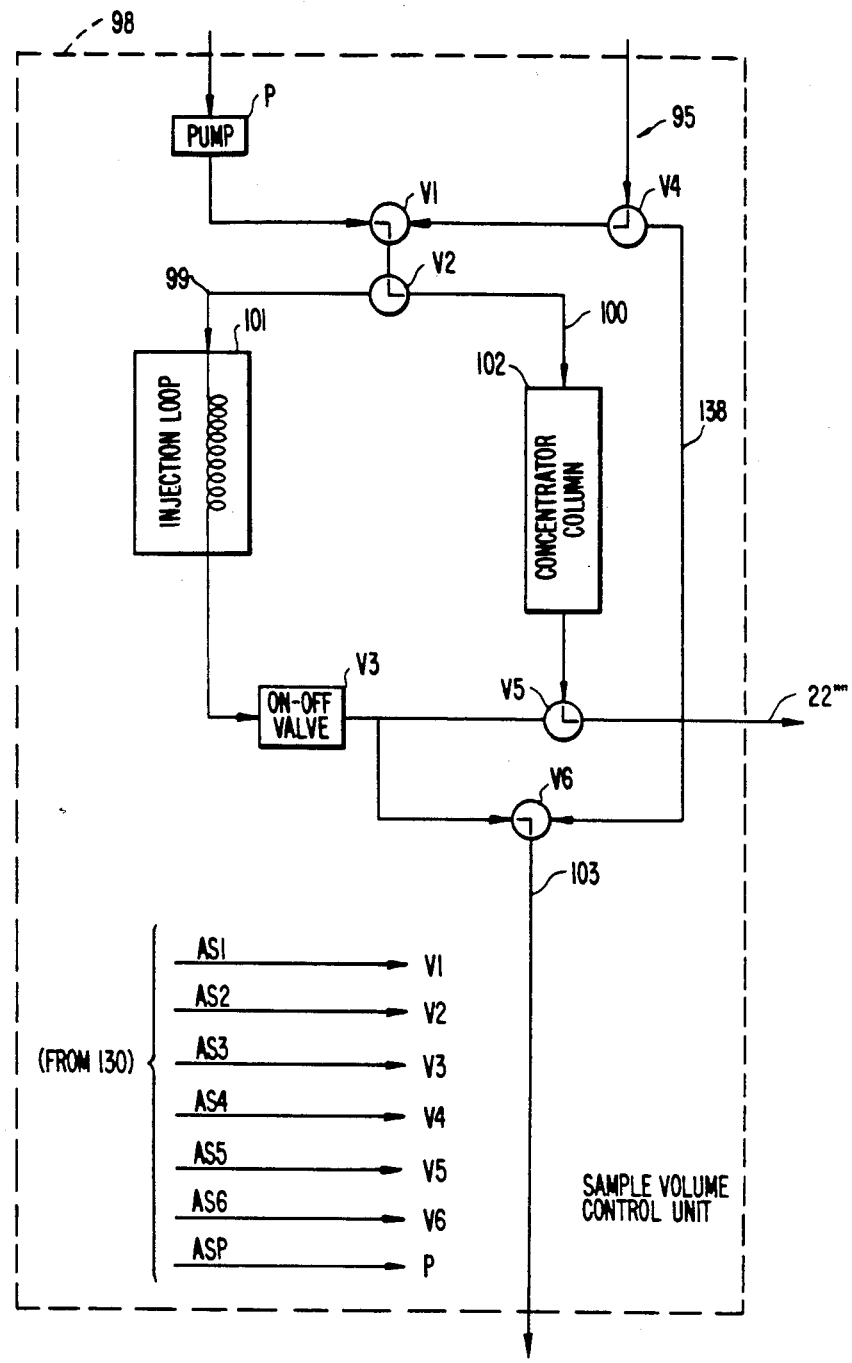
FIG. 5 is a diagram of a sample volume control unit of one chromatograph in the ion chromatograph unit in FIG. 3.

FIG. 5 is a block diagram of a standard valve arrangement employed in the sample volume control unit 98 to prepare a sample volume of an influent fluid sample stream for analysis. The sample volume control unit 98 comprises a pump P for supplying the influent fluid sample stream at a predetermined volumetric rate in accordance with an activation signal ASP, and valves V1–V6 selectively operable in accordance with actuation signals AS1–AS6 to establish one of five flow paths FP1–FP5: the first flow path FP1 extends from the pump P through the injector loop 101 to valve V3; the second flow path FP2 extends from the pump P through the concentrator column 102 to a drain 22""; the third flow path FP3 extends from the eluant supply line 95 through the injection loop 101 to the separator column 104 (FIG. 3); the fourth flow path FP4 extends from the eluant supply line 95 through the concentrator column 102 to the separator column 104; and the fifth flow path FP5 extends from the eluant supply line 95 to the separator column 104. The pump P provides the influent fluid samples stream at a known volumetric rate of flow and the pump 96 in the eluant supply system 89 provides the eluant at a known volumetric rate of flow so that control of the valves V1–V6 to establish flow paths FP-1–FP-5, and control of pump P and pump 96 as a function of time provides a specific volume of an influent fluid sample stream or an eluant. Actuation signals AS1–AS6 and ASP comprise sample volume control means actuator signals.

Upon a determination that the calculated, required volume of the influent fluid sample to be prepared for analysis, the "sample volume", is the injection loop volume, the injection loop volume being defined as the combined volume of the first parallel fluid line 99 and the injection loop 101, actuation signals AS1–AS6 are generated to establish flow path FP1. In particular, actuation signals AS1 and AS2 are generated to actuate valves V1 and V2 to provide the influent fluid sample stream to the injection loop 101, and actuation signal AS3 is generated to close valve V3. Then, actuation signal ASP is generated to operate pump P until the injection loop 101 and the first parallel fluid line 99 are filled with the influent fluid sample. Of course, the time necessary to fill the injection loop 101 and the first parallel fluid line 99 can be calculated from the known injection loop volume and the known volumetric flow rate provided by pump P. After the injection loop 101 and the first parallel fluid line 99 are filled with the influent fluid sample actuation signals AS1, AS4 and AS6 are generated to establish flow path FP3, and then actuation signal AS3 is generated to open valve V3 and pump 96 is actuated so that an eluant moves the sample volume of the influent fluid sample, which is equal to the injection loop volume, through the separator column 104, the suppressor column 106, and the detector 108.

Upon a determination that the sample volume is greater than the injection loop volume, but limited to a maximum load value, valves V1–V6 are operated to sequentially establish flow paths FP2 and FP4. First, actuation signal AS3 is generated to close valve and V3, Then, actuation signals AS1, AS2, and AS5 are generated to operate valves V1, V2, and V5 to supply the influent fluid sample stream to the concentrator column 102 and then to the drain 22"", thereby establishing flow path FP2. After flow path FP2 has been established, actuation signal ASP is generated to operate pump P for a time which provides the sample volume of the influent fluid sample stream. In this manner the sample volume of influent fluid sample stream is passed through the concentrator column 102 and the ions in the influent fluid sample stream are collected in a resin (not shown) in the concentrator column 102. When the ions from the predetermined volume of the influent fluid sample have been collected in the resin, actuator signals AS1, AS4 and AS5 are generated to actuate valves V1, V4 and V5 to establish flow path FP4 and the pump 96 is actuated to supply an eluant through eluant supply line 95 at a predetermined volumetric rate. The eluant passes through the resin in the concentrator column 102 and carries the ions accumulated in the resin to the separator column 104, the suppressor column 106 and the detector 108.

If it is desired to supply an eluant directly to the separator column 104, actuation signals AS4 and AS6 are generated to establish flow path FP5. Then, pump 96 is actuated to supply an eluant through supply line 95, supply line 138, and chromatograph fluid line 103 to the separator column 104.

Figure 6:
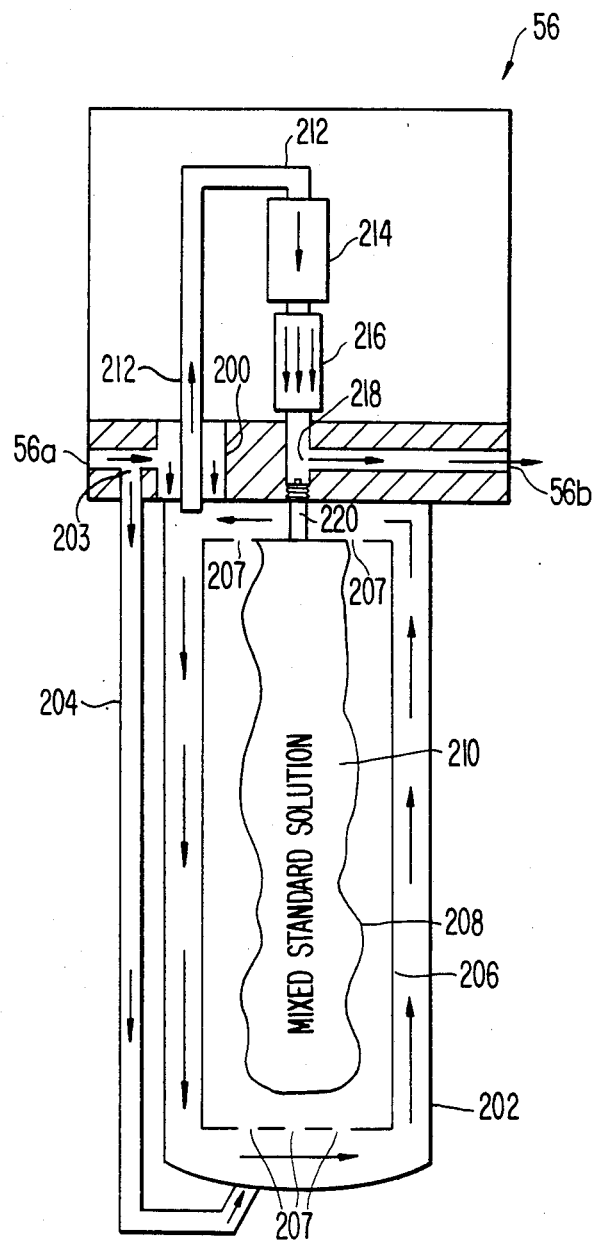
FIG. 6 is a diagram of a conditioning unit in the continuous monitor module of FIG. 2.

FIG. 6 is a diagram of the conditioning unit 56 in the calibration unit 48 shown in FIG. 2. The conditioning unit 56 may be an AQUAprep Chemical Injection System produced by Barnstead. The AQUAprep has been used to add chemicals to a fluid stream for purposes such as pH adjustment, chlorination, and dechlorination, the specific chemicals for these purposes being sulphuric acic ($H_2SO_4$), sodium hypochlorite (NaOCl), and sodium bisulphite ($NaHSO_3$), respectivley. The AQUAprep, however, has not been used to inject chemicals for the purpose of conditioning a fluid stream to calibrate chemical monitors. Further, the AQUAprep must be modified by substituting an appropriate mixed standard solution (described below) for the pH adjusting, chlorination, or dechlorination chemicals originally provided with the AQUAprep. In addition, the fluid flow of the AQUAprep has been modified to stabilize the chemical characteristics of the conditioned fluid sample.

The operation of the conditioning unit 56 is as follows. The second portion of the influent fluid sample stream, the deionized second portion of the influent fluid sample stream, enters the calibration unit 56 at the input 56a thereof and flows downward through an outer concentric tube 200 into a cartridge housing 202. It has been determined that modifying the AQUAprep, by adding a T-junction 203 and an external fluid line 204 to supply a portion of the influent fluid sample stream to the bottom of the cartridge housing 202, stabilizes the chemical characteristics of the conditioned fluid sample stream by causing all of the fluid in the cartridge housing 202 to be exchanged. The influent fluid sample stream in the cartridge housing 202 enters a cartridge 206 via holes 207 therein, and surrounds and pressurizes a flexbile, two-ply plastic bag 208 containing a mixed standard solution 210. The flexibility of the plastic bag 208 assures that the pressure on the mixed standard solution 210 is exactly the same as the water pressure of the influent fluid sample stream outside of the bag 208. Further, there is no stress on the bag 208 because it simply defines a relaxed boundary between two liquids. The influent fluid sample stream then flows upward from the cartridge housing 202 through an inner concentric tube 212 to a fine adjustment valve 214, and then to a laminar flow element 216. The laminar flow element 216 creates a pressure differential by changing the turbulent flow of the influent fluid sample stream to laminar flow at the output of the laminar flow elment 216. This pressure differential causes the mixed standard solution 210 in the bag 208 to be injected into the influent fluid sample stream at a mixing point 218 through a flow restrictor 220 attached to the bag 208 and having a flow-restricting capilliary tube therein. Since the pressure differential is created by establishing a laminar flow of the influent fluid sample stream, and because the pressure in a fluid stream having laminar flow varies directly with flow rate, a change in the flow rate of the influent fluid sample stream produces a corresponding change in the injection rate of the mixed standard solution, and the dilution ratio of the mixed standard solution 210 in the influent fluid sample stream remains constant. Thus, the pressure of the influent fluid sample stream has no effect on the injection of the mixed standard solution; the injection rate is only affected by the pressure drop created by the laminar flow element 216. The substitution of various flow restrictors 220 provides injection rates of approximately 0.5 ppm to approximately 160 ppm. In addition, the 90° turn at the mixing point 218 provides for mixing of the mixed standard solution in the influent fluid sample stream.

The composition of the mixed standard solution 210 is dependent on the monitors which are being calibrated and the concentration of the chemicals in the mixed standard solution are varied in accordance with the injection rate to provide a conditioned influent fluid sample stream having chemical characteristics in the range of the chemical characteristics that the monitors are monitoring. In particular, by adding ammonium hydroxide (NH$_4$OH), sodium chloride (NaCl), and hydrazine (N$_2$H$_4$), pH, specific conductivity, ammonia, cation conductivity, sodium, and hydrazine monitors can be calibrated. The concentration of ammonium hydroxide in the mixed standard solution is dictated by the range in which the pH monitor is to be calibrated. Most power plants operate with steam cycle water having a pH of approximately 9.5. Thus, the concentration of ammonium hydroxide in the mixed standard solution is adjusted in accordance with the injection rate and the flow rate of the influent fluid sample stream established by flowmeter 60 (FIG. 2) so that the conditioned influent fluid sample stream contains approximately 1.5 ppm of ammonium hydroxide to yield a pH of approximately 9.5. The ammonium hydroxide concentration is also directly related to the specific conductivity of the conditioned influent fluid sample stream—1.5 ppm of ammonium hydroxide yielding a specific conductivity of approximately 8 $\mu$mhos. An ammonium monitor can be calibrated directly from the known concentration of ammonia (in ppm) in the conditioned influent fluid sample stream. The concentration of sodium chloride in the mixed standard solution is adjusted in accordance with the injection rate and flow rate so that the conditioned influent fluid sample stream has a concentration of approximately 33 ppb of sodium chloride. A concentration of 33 ppb of sodium chloride results in a chloride (Cl$^-$) concentration of 20 ppb and a sodium (Na$^+$) concentration of 13 ppb. The chloride concentration is related to cation conductivity and a sodium monitor can be calibrated a known concentration (in ppb) of sodium. If hydrazine is added to the mixed standard solution, the concentration of hydrazine in the mixed standard solution 210 should be selected to yield a concentration of approximately 50 ppb of hydrazine in the conditioned influent fluid sample stream. However, it may not be desirable to add hydrazine to the mixed standard solution 210 because it is a toxic chemical. Other species such as sulfate (SO$_4$--), in the form of sulfuric acid, copper (Cu), iron (Fe), and flouride (F$^-$) in the form of soluable salts, and organic acids, for example, acetic acid and formic acid, may be included in the mixed standard solution in order to calibrate the ion chromatograph unit 42.

It has been determined that high concentrations of ammonium hydroxide in the mixed standard solution cause the ammonium hydroxide to diffuse through the plastic bag 208, resulting in cracking of the cartridge 206. Thus, it is desirable to use a lower concentration of ammonium hydroxide in conjunction with a higher injection rate or to replace the bag 208 with a bag which is not permeable to higher concentrations of ammonium hydroxide.

The operation of the continuous on-line water chemistry monitor system of the present invention will be described with reference to the flowcharts in FIGS. 7–16.

Figure 7A:
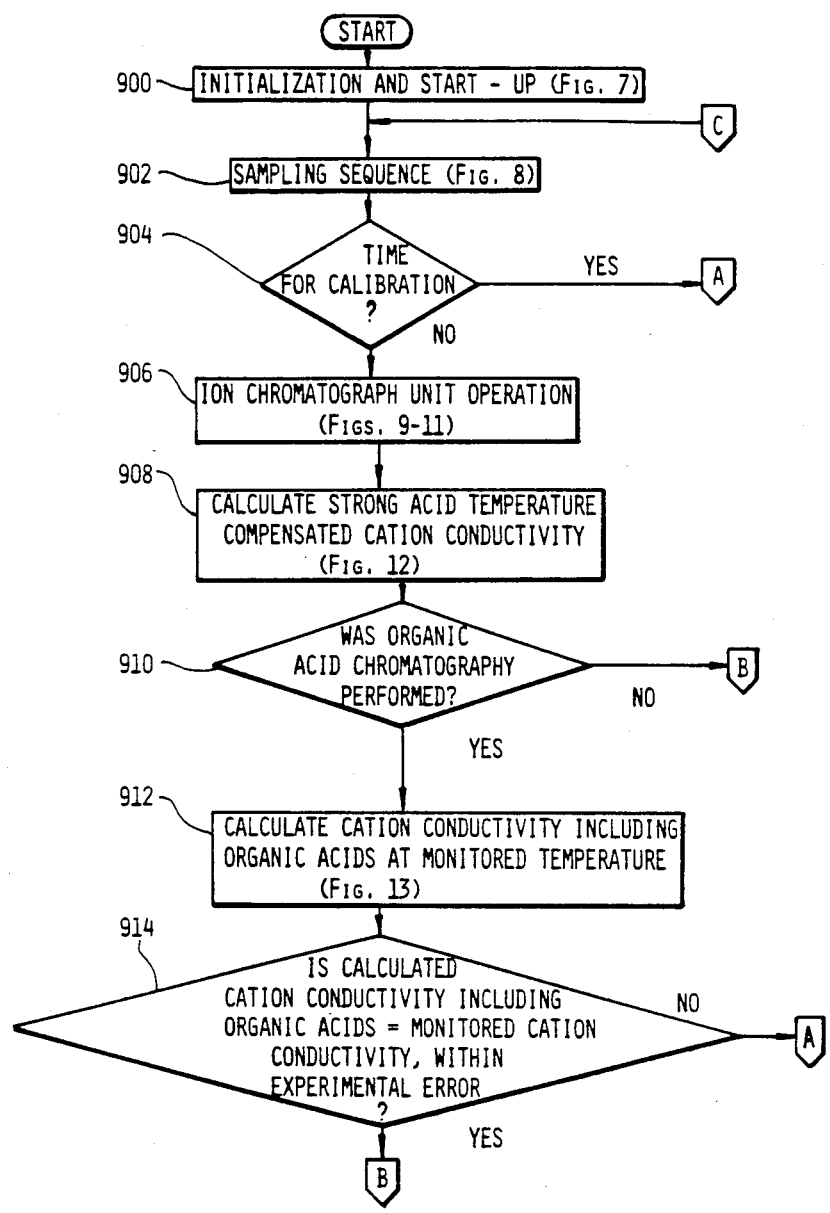
FIGS. 7a, 7b, and 8-16 are flowcharts for describing the operation of the monitoring system of the present invention.
Figure 7B:
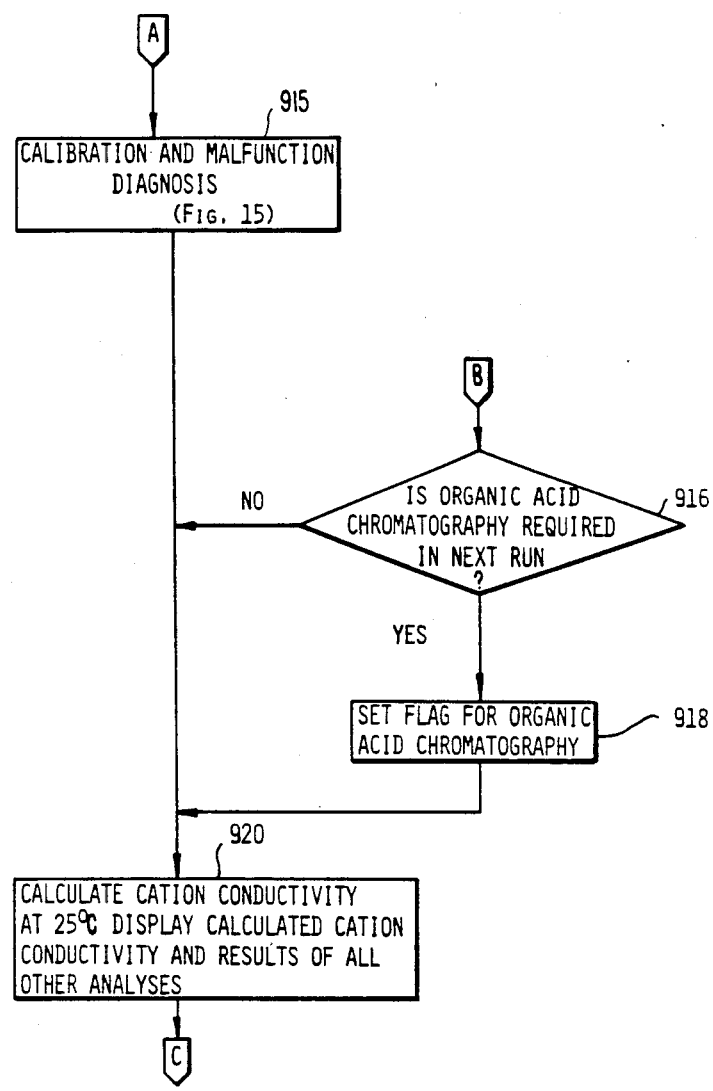

FIGS. 7A and 7B are flowcharts showing the overall operation of the system of the present invention.

Step 900: Initialization and start-up of the system, including selecting analyses to be performed in the initial run, as shown in detail in FIG. 8.

Step 902: Determination of the sampling sequence for the first and second valve systems 34, 38, i.e., the order in which the first and second valve systems 34, 38 supply the third and fourth influent fluid sample streams to the ion chromatograph unit 42, as shown in detail in FIG. 9.

Step 904: Determine if a predetermined calibration interval has elapsed. If the calibration interval has elapsed, calibration is to be performed and processing proceeds to step 915. If calibration is not to be performed, processing proceeds to step 906.

Step 906: Operation of the ion chromatograph unit 42 to perform anion chromatography, organic acid chromatography, and cation chromotography, as shown in detail in FIGS. 10–12.

Step 908: Calculation of a strong acid temperature compensated cation conductivity based on the monitored temperature of the influent fluid sample stream analyzed by the ion chromatograph unit, predetermined conductivity equations, and the ions detected by anion chromatography and cation chromatography.

Step 910: Determine if organic acid chromatography was performed.

Step 912: If organic acid chromatography was performed, calculate cation conductivity including organic acids at the monitored temperature, as shown in detail in FIG. 14.

Step 914: Determine if the calculated cation conductivity including organic acids is approximately equal to the monitored conductivity. If these two values do not correspond within experimental error, processing proceeds to step 905 for calibration. If these values do not correspond, processing proceeds to step 915; if these values do correspond, processing proceeds to step 916.

Step 915: If it is determined, in step 904, that calibration is to be performed, calibration and malfunction diagnoses are performed, as shown in detail in FIG. 16.

Step 916: Determine if organic acid chromatography is required in the subsequent run by comparing the strong acid temperature compensated cation conductivity with the monitored cation conductivity. If these valves are not approximately equal, it is determined that organic acid chromatography is to be performed on the next third influent fluid sample stream to be supplied to the ion chromatograph unit 42.

Step 918: If organic acid chromatography is determined to be required in the next run, a flag is set for organic acid chromatography.

Step 920: A cation conductivity for 25° C. is calculated, and the calculated conductivity at 25° C. and the results of all other analyses are displayed. Processing then returns to step 902.

Figure 8:
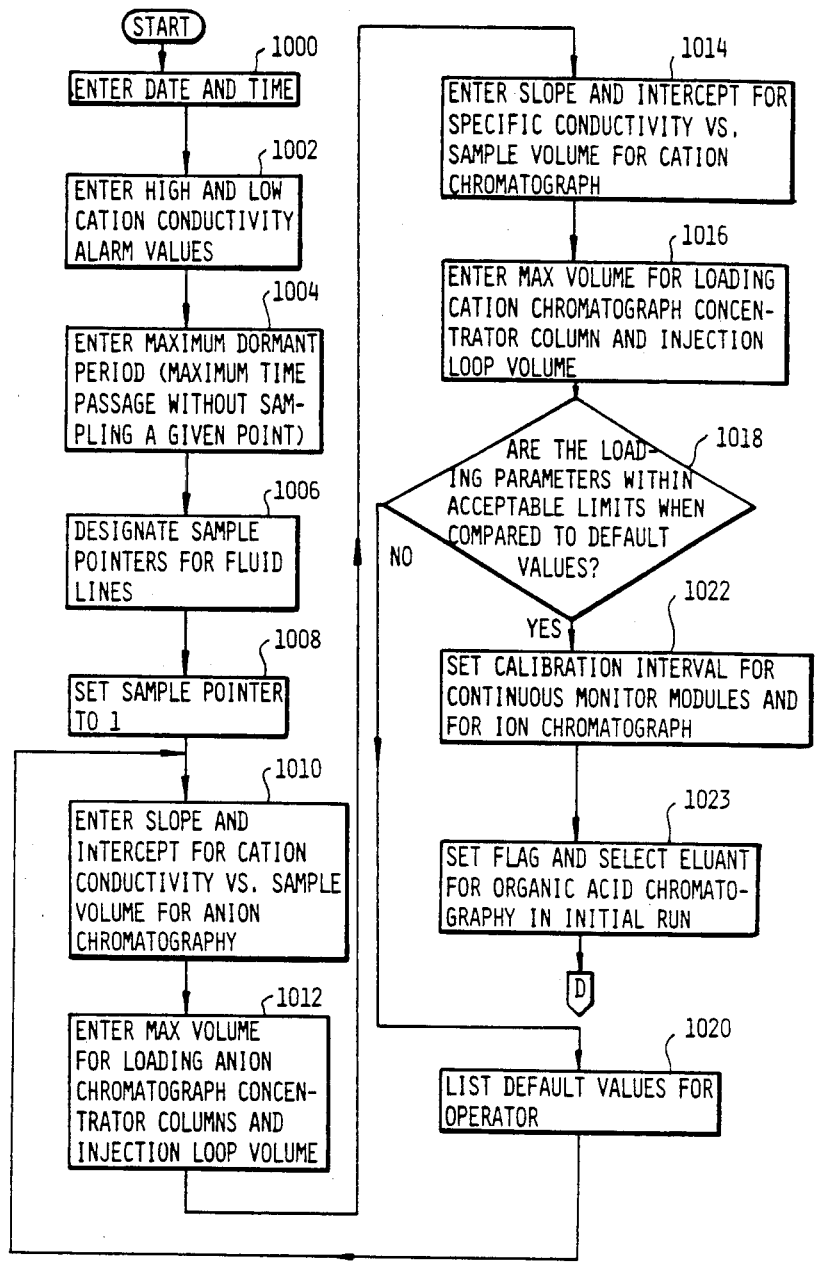

FIGS. 8–16 are flowcharts detailing the operations shown in the flow chart of FIG. 7. In particular, FIG. 8 is a flow chart illustrating the initialization and start-up procedure.

Step 1000: Enter date and time.

Step 1002: Enter high and low cation conductivity alarm values.

Step 1004: Enter maximum dormant period, i.e., the maximum time between ion chromatographic analysis of the influent fluid sample stream supplied by a particular one of the fluid lines 10. The maximum dormant period may be set at, for example, one day (24 hours).

Although the maximum period between the ion chromatograph analyses of a particular sample may be as long as 24 hours, the continuous monitors 68–73 in each continuous monitor module 20, as well as the cation conductivity monitors 32, provide continuous on-line monitoring of each influent fluid sample stream. Further, it is unlikely that the maximum dormant period will elapse between chromatographic analyses of a particular influent fluid sample stream since the time necessary for each run of the ion chromatograph unit 42 is approximately one half hour.

Step 1006: Designate sample pointers with corresponding fluid lines $10_1, 10_2, \ldots 10_n$.

Step 1008: Set sample pointer to 1.

Step 1010: Enter slope and intercept values from a known equation describing the relationship between the cation conductivity and the concentration of anions and organic acids in a fluid sample. This equation is used to determine the volume of a fluid sample necessary to provide the quantity of anions or organic acids which are necessary for accurate chromatographic analysis, i.e., the "sample volume" for the anion chromatograph 86.

Step 1012: Enter maximum volume for loading the anion chromatograph concentrator column 102. Enter the injection loop volume for the anion chromatograph 86.

Step 1014: Enter slope and intercept values for a known equation describing the relationship of the specific conductivity and the concentration of cations in a fluid sample. This equation is used to determine the volume of a fluid sample necessary to provide the quantity of cations necessary for accurate cation chromatography, i.e., the "sample volume" for the cation chromatograph.

Step 1016: Enter maximum volume for loading cation chromatography concentrator column. Enter the injection loop volume for the cation chromatograph 88.

Step 1018: Determine if the maximum loading volumes and injection loop volumes for all chromatographs 86–88 are within acceptable limits when compared to default values.

Step 1020: List default values on display 95 or printer 96, shown in FIG. 4, if the loading parameters are not within the acceptable limits when compared with default values and return to step 1010.

Step 1022: Set calibration interval for continuous monitor modules 20 and for the ion chromatograph unit 42.

Step 1023: Set flag and select eluant for organic acid analysis in initial run, and proceed to flow D (FIG. 9).

Figure 9:
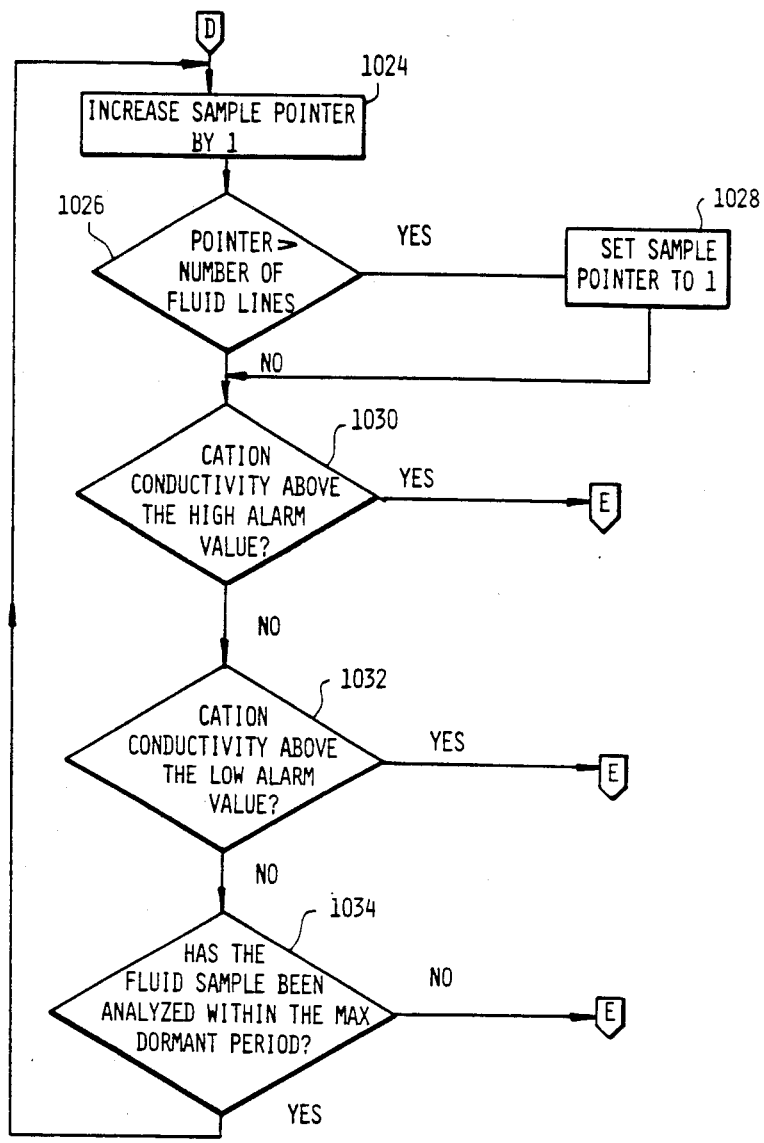

FIG. 9 is a flowchart describing the determination of the sequence in which the influent fluid sample streams, supplied by each of the fluid lines 10, are provided to the ion chromatograph unit 42.

Step 1024: Increase sample pointer by 1.

Step 1026: Determine if sample pointer value is greater than the number n of fluid lines 10.

Step 1028: Set pointer to 1 if the pointer value is greater than the number n of fluid lines 10. From this point processing is performed for the influent fluid sample stream supplied by the fluid line 10 corresponding to the sample pointer value.

Step 1030: Determine if the monitored cation conductivity is above the high alarm value set in step 1002. If the monitored cation conductivity value is above the high alarm value processing proceeds to flow E (FIG. 10).

Step 1032: Determine if the monitored cation conductivity is above the low alarm value. If the cation conductivity is above the low alarm value, processing proceeds to flow E. If the cation conductivity is not above the low alarm value, it is determined that the influent fluid sample stream does not contain a high enough concentration of ions to justify performing chromatographic analysis.

Step 1034: Determine if the influent fluid sample stream associated with the selected fluid line 10 has been analyzed within the maximum dormant period set in step 1004. If the fluid sample has not been analyzed within the maximum dormant period, processing proceeds to flow E. If the fluid sample has been analyzed within the maximum dormant period, processing returns to step 1024.

Figure 10:
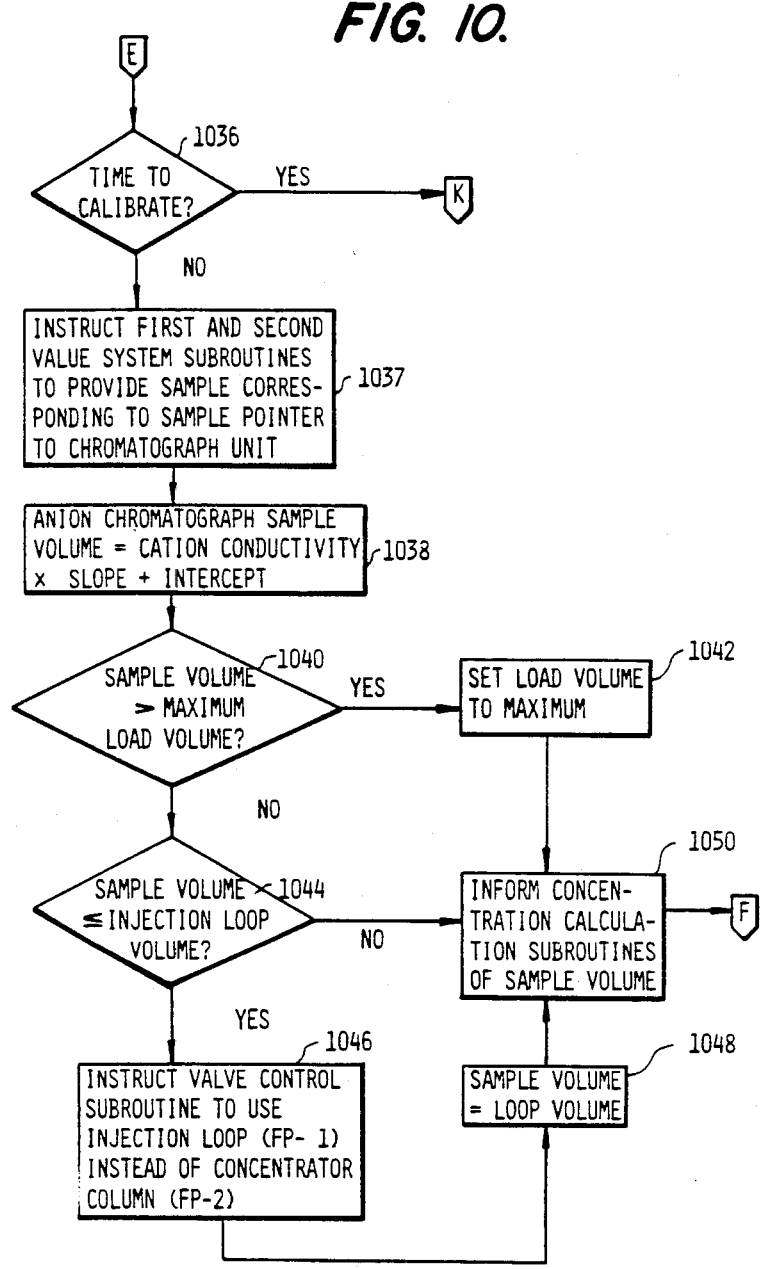
Figure 11:
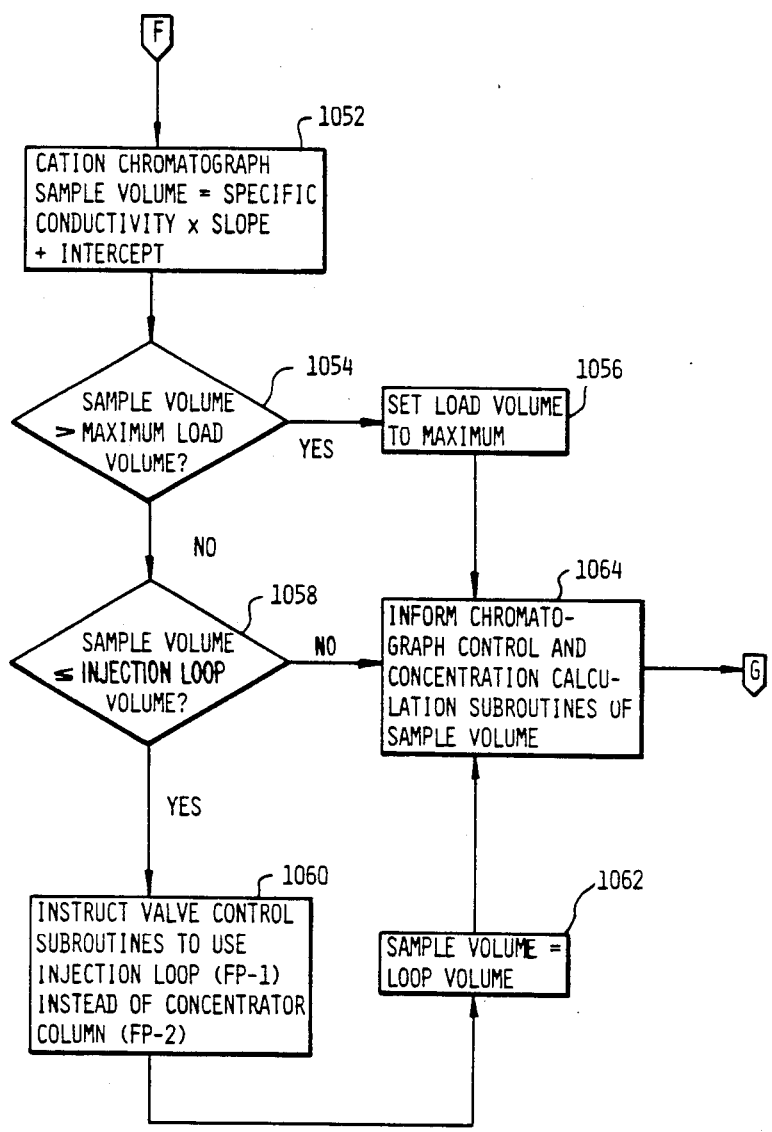
Figure 12:
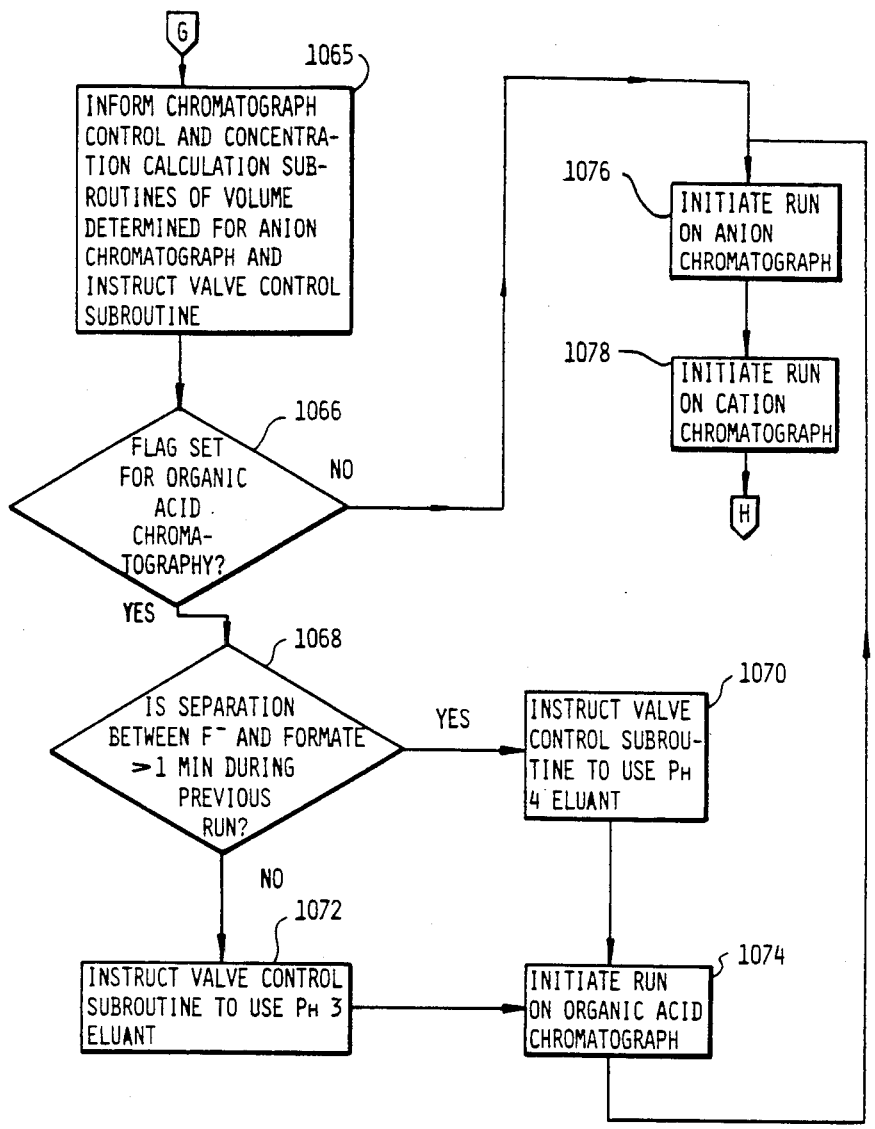

The flow charts of FIGS. 10–12 provide an illustration of the control of the operation of the ion chromatograph unit 42.

Step 1036: Determine if the calibration interval has elapsed. If the interval has elapsed, processing proceeds to flow K, shown in FIG. 16, for calibration.

Step 1037: Instruct first and second valve system subroutines to provide the altered third and fourth fluid sample streams corresponding to the influent fluid sample stream supplied by the fluid line 10 corresponding to the sample pointer to the ion chromatograph unit 42. The first and second valve system subroutines can be generated by one of ordinary skill in the art in accordance with the disclosure in U.S. Pat. No. 4,414,858, previously incorporated by reference.

Step 1038: Calculate an anion chromatograph sample volume with predetermined equations, particularly by multiplying the monitored cation conductivity with the slope entered in step 1010 and then adding the intercept value entered in step 1010.

Step 1040: Determine if the calculated sample volume is greater than the maximum load volume for the anion chromatograph concentrator column entered in step 1012. If the calculated sample volume is greater than the maximum load volume, processing proceeds to step 1042; otherwise, processing proceeds to step 1044.

Step 1042: Set anion chromatograph sample volume to the maximum load volume if the calculated sample volume is greater than the maximum load volume, then proceed to step 1050.

Step 1044: Determine if the calculated sample volume is less than or equal to the injection loop volume set in step 1012. If the calculated sample volume is greater than the injection loop volume, processing proceeds to step 1050. If the calculated sample volume is less than or equal to the injection loop volume, processing proceeds to step 1046.

Step 1046: Instruct a valve control subroutine for the anion chromatograph 86 sample volume control unit 98 to use the injection loop 101 (FP-1) instead of the concentrator column 102 (FP-2), if the calculated sample volume is less than or equal to injection loop volume. The valve control subroutine can easily be developed by one of ordinary skill in the art in accordance with the description of the operation of the sample volume control unit 98 previously provided.

Step 1048: Set sample volume to the loop volume.

Step 1050: Inform concentration calculation subroutines of the sample volume, i.e., the calculated sample volume if it is greater than the injection loop volume and less than the maximum load volume, the maximum load volume set in step 1042 if the calculated sample volume is greater than the maximum load volume, or the loop volume set in step 1048 if the calculated sample volume is less than or equal to the injection loop volume. The concentration calculation subroutines can be developed by one of ordinary skill in the art based on the operation of standard chromatographs. After the anion chromatograph sample volume is determined, processing proceeds to flow F (FIG. 11).

Step 1052: Calculate cation chromatograph sample volume with predetermined equations, particularly by multiplying the monitored specific conductivity with the slope entered in step 1014 and then adding the intercept value entered in step 1014.

Step 1054: Determine if the calculated cation chromatograph sample volume is greater than the maximum load volume set in step 1016. If the calculated sample volume is grater than the maximum load volume, processing proceeds to step 1056; otherwise, processing proceeds to step 1058.

Step 1056: Set cation chromatograph sample volume to maximum load volume if the calculated sample volume is greater than the maximum load volume.

Step 1058: Determine if the calculated sample volume is less than or equal to the injection loop volume set in step 1016.

Step 1060: Instruct cation chromatograph sample volume control unit (not shown) valve control subroutine to use an injection loop (FP-1) instead of a concentrator column (FP-2), if the calculated sample volume is less than or equal to the injection loop volume.

Step 1062: Set sample volume to the injection loop volume.

Step 1064: Inform concentration calculation subroutine of the sample volume. After the cation chromatograph sample volume is determined, processing proceeds to flow G (FIG. 12).

Step 1065: Set the organic acid chromatograph sample volume to the anion chromatograph sample volume and instruct valve control and concentration calculation subroutines accordingly.

Figure 15:
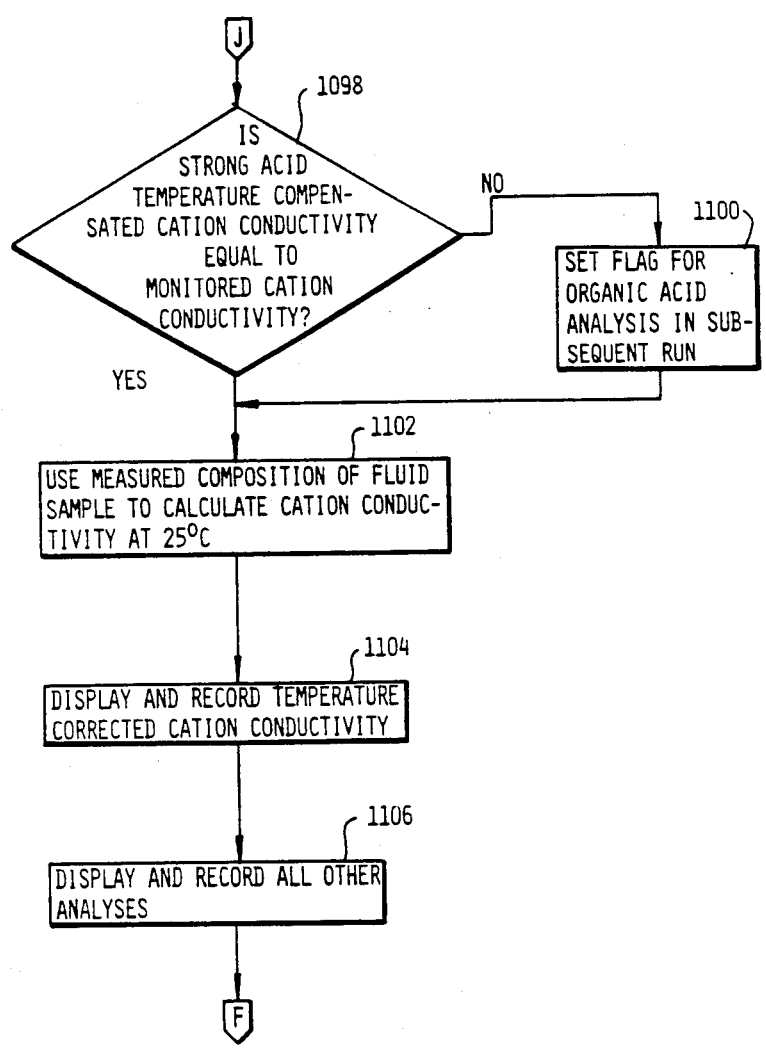

Step 1066: Determine if the flag is set for an organic acid analysis. For the initial run, the flag is set in step 1023, and for subsequent runs the flag for organic acid analysis is set in the processing of flow J (FIG. 15). If the organic acid analysis flag is not set, processing proceeds to step 1076.

Step 1068: Determine if the time for the separation of flouride ($F^-$) and formate (an anion often found in power plant steam cycle water) which occurs in the organic acid chromatograph separator column (not shown), is greater than one minute during the previous run of the organic acid chromatograph 87 in order to select the appropriate eluant. In the initial run the eluant is selected in step 1023. The separation time is determined by the order of the peaks for flouride and formate in the analysis of the previous run, and one of ordinary skill in the art would be able to instruct the control system to determine the order of the peaks automatically.

Step 1070: If the separation time during the previous run was greater than one minute, a valve control subroutine for the eluant supply system 89 is instructed to supply a pH 4 eluant. One of ordinary skill in the art would be able to develop a valve control subroutine for actuating the eluant selector valve 94 to select a pH 3 or pH 4 eluant.

Step 1072: If the separation time during the previous run was one minute or less, the valve control subroutine for the eluant supply system 89 is instructed to supply a pH 3 eluant.

Step 1074: Initiate organic acid chromatography.

Step 1076: Initiate anion chromatography.

Step 1078: Initiate cation chromatography and then proceed to flow H (FIG. 13).

Figure 13:
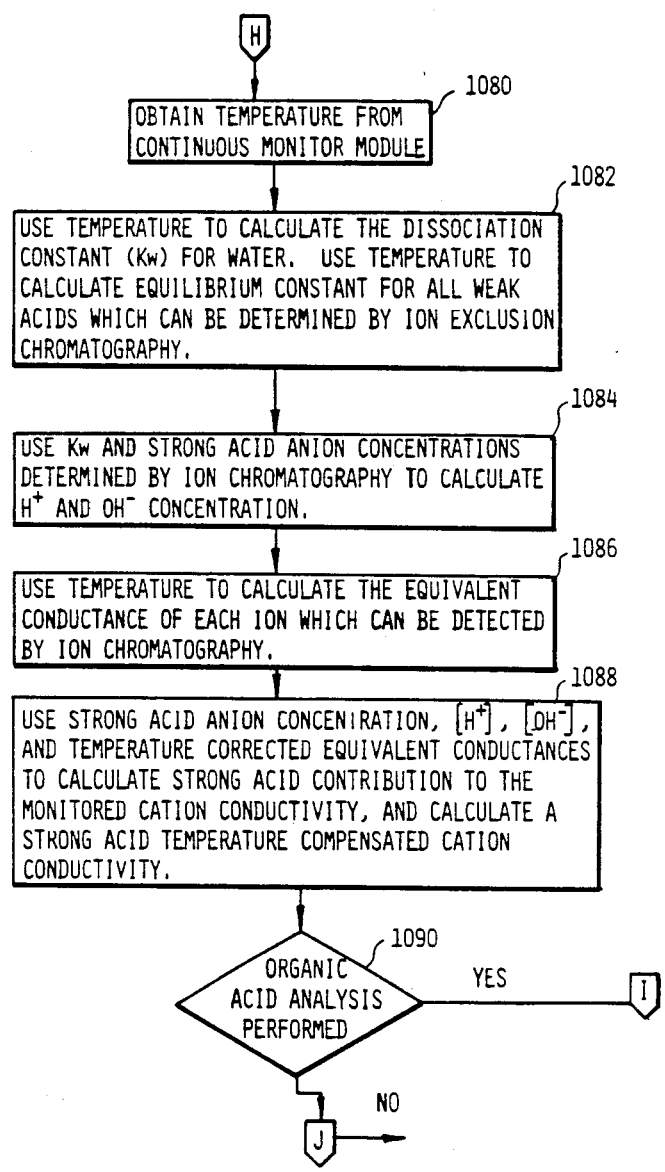

The flow chart of FIG. 13 relates to the calculation of a strong acid temperature compensated cation conductivity using predetermined conductivity equations.

Step 1080: Obtain the monitored temperature of the fluid sample undergoing chromatographic analaysis from the corresponding continuous monitor module 20.

Step 1082: Calculate the dissociation constant for water (Kw) using the monitored temperature obtained in step 1080 and a value obtained from a computer resident look-up table based on data presented in a table of Ionization Constants for water (Kw) presented in the Handbook of Chemistry and Physics, 56th Ed., (CRC Press, Cleveland 1975), page D-152. Calculate the equilibrium, or inonization constants for all weak acids which can be determined by ion exclusion chromatography using the monitored temperature and values obtained from a computer resident look-up table based on data presented in a table of Ionization Constants of Acids in Water at Various Temperatures presented in the Handbook of Chemistry and Physics at page D-152.

Step 1084: Calculate H+ and OH− concentrations using the dissociation constant Kw and strong acid anion concentrations determined by ion chromatography by solving the following equations (1)–(5) simultaneously:

$$K_w = [H^+][OH^-] \quad (1)$$

$$K_{Ai} = \frac{[H^+][A_i^-]}{[HA_i]} \quad (2)$$

wherein Kw = is the equlibrum contant for water at the monitored termperature;

$K_{Ai}$ is the equilibrium constant for the with weak acid, $HA_i$, which has been determined by organic acid chromatography;

[H+] is the concentration of the hydrogen ion;

[$A_i^-$] is the concentration of the conjugate base of the ith acid, HA;

[$HA_i$] is the concentration of the ith acid, $HA_i$; and

[OH−] is the concentration of the hydroxide ion.

$$[H^+] = [OH^-] + \sum_{i=1}^{n}[A_i^-] + \sum_{j=1}^{m}[B_j^-] \quad (3)$$

wherein n is the number of weak acids determined by organic acid chromatograph; and m is the number of strong acid anion concentrations determined by ion chromatography.

Mass Balance Equations $$F_i = [HA_i] + [A_i^-] \quad (4)$$

$$F_j = [B_j^-]. \quad (5)$$

Step 1086: Calculate the equivalent conductance for each ion which can be detected by ion chromatography using the monitored temperature obtained in step 1080 and values obtained from a computer resident look-up table based on the data presented in a table of the Equivalent Conductance Separate Ions presented in the Handbook of Chemistry and Physics at page D-153.

Step 1088: Calculate the strong acid contribution to the monitored cation conductivity using strong acid anion concentrations, [H+], [OH−], and the temperature corrected equivalent conductances, and calculate a strong acid temperature compensated cation conductivity using the temperature corrected equivalent conductances and equation (6) below.

$$cc = [H^+]\lambda_{H+} + [OH^-]\lambda_{OH-} + \sum_{i=1}^{n}[A_i^-]\lambda_i + \sum_{i=1}^{m}[B_j^-]\lambda_j \quad (6)$$

wherein cc is the cation conductivity;

$\lambda_{H+}$ is the equivalent conductance of the hydrogen ion;

$\lambda_{OH-}$ is the equivalent conductance of the hydroxide ion;

$\lambda_i$ is the equivalent conductance of the conjugate base of the ith weak acid; and $\lambda_j$ is the equivalent conductance of the jth strong anion.

Since the concentrations of the weak acids determined by organic acid chromatograph are represented by [$A_i^-$] and [$HA_i$], only equations (1), (3) and (5) must be solved to calculate the strong acid anion concentrations for the strong acids determined by anion chromatography. Thus, to determine the strong acid anion concentrations, [$A_i^-$]=0 for all i.

To obtain the cation conductivity which includes both weak acid and strong acid anion concentrations, equations. (1)–(6) are solved simultaneously for cc.

Step 1090: Determine if organic acid analysis was performed during the run. If organic acid analysis was performed processing proceeds to flow G, and if organic acid analysis was not performed, processing proceeds to flow I (FIG. 14).

Figure 14:
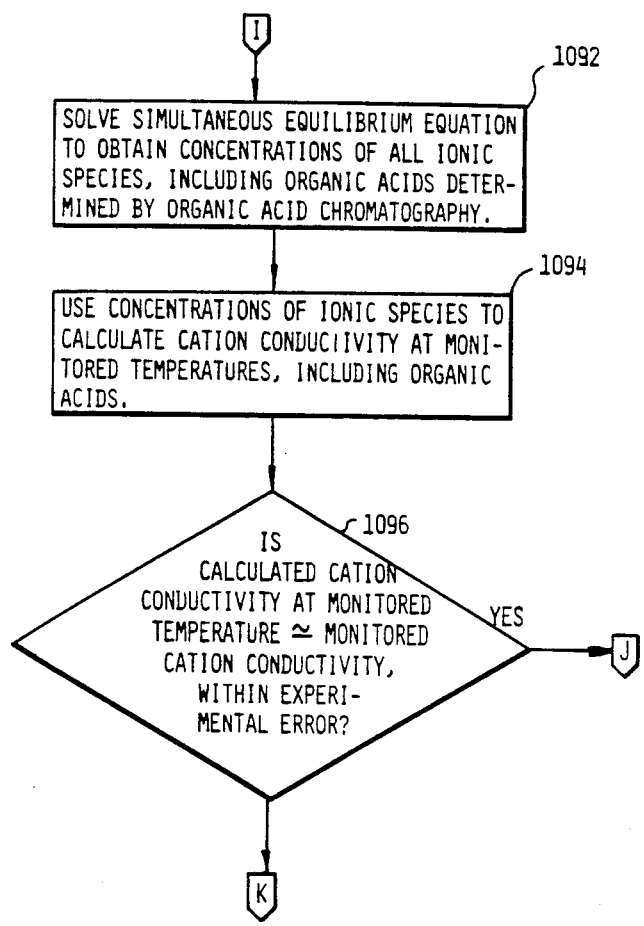

The flowchart of FIG. 14 relates to the calculation of a cation conductivity, including the organic acid concentrations determined by organic acid chromatography, at the monitored temperature.

Step 1092: Obtain concentrations of all of the ionic species, including organic acids, determined by ion chromatography by solving equations (1)–(5) including all Fi values obtained by organic acid chromatography.

Step 1094: Calculate cation conductivity at monitored temperature using concentrations of ionic species, including organic acids, obtained in step 1092.

Step 1096: Determine if the calculated cation conductivity at the monitored temperature, including organic acids, is approximately equal to the monitored cation conductivity, within the range of experimental error. If the calculated cation conductivity at the monitored temperature is not approximately equal to the monitored conductivity, processing proceeds to flow K (FIG. 16) for calibration. If the calculated cation conductivity at the monitored temperature is approximately equal to the monitored cation conductivity, processing proceeds to flow J (FIG. 15).

Step 1098: Determine if strong acid temperature compensated cation conductivity is approximately equal to the monitored cation conductivity. If these two values are not approximately equal, it is determined that organic acid analysis is required in the next, or subsequent, run and processing proceeds to step 1100; otherwise, processing proceeds to step 1102.

Step 1100: Set flag for organic acid analysis in subsequent run.

Step 1102: The measured composition of the sample fluid is used to calculate the cation conductivity at 25° C. This prediction is based on known parameters referenced in step 1082.

Step 1104: Display and record temperature corrected cation conductivity.

Step 1106: Display and record all other analytical results and proceed to flow D (FIG. 9) to perform subsequent run.

Figure 16:
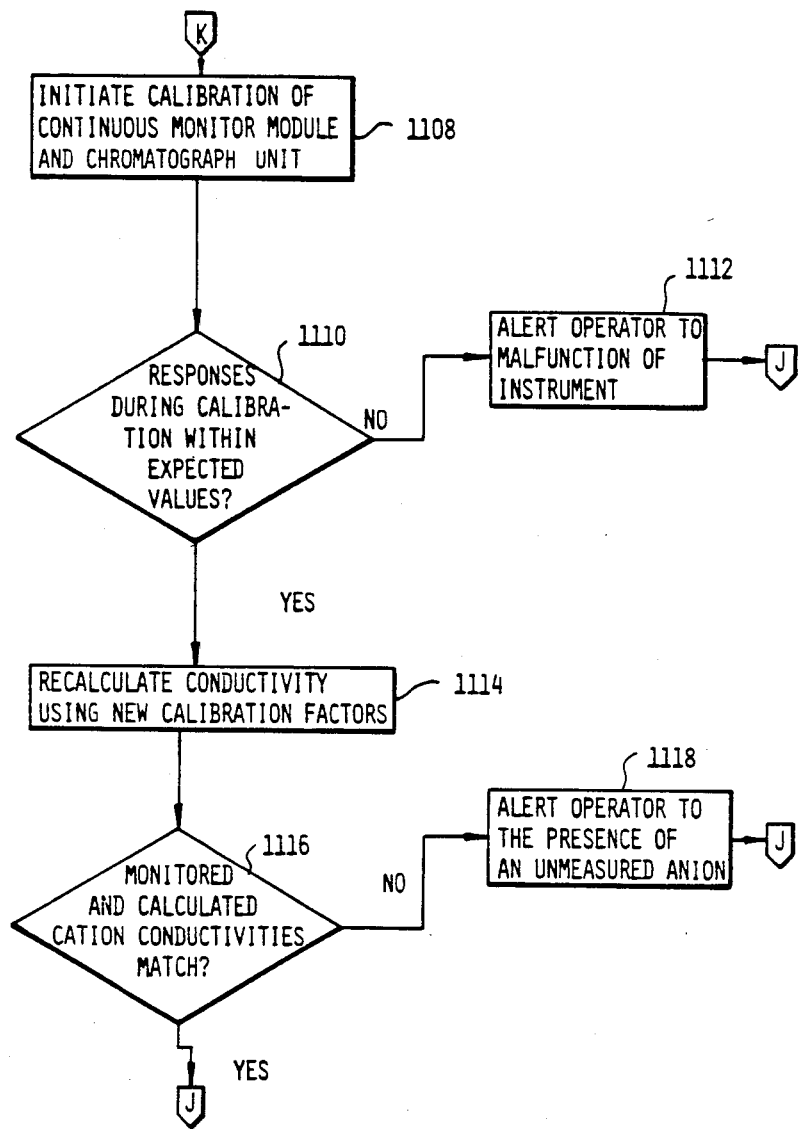

Flow K, shown in FIG. 16, relates to calibration and malfunction diagnosis.

Step 1108: If the calculated cation conductivity is not determined to be approximately equal to the detected conductivity at step 1096, the calibration subroutine is instructed to calibrate the continuous on-line monitors 68–73 in the continuous monitor module 20 corresponding to the influent fluid sample stream being analyzed during the run and the ion chromatograph unit 42. The corresponding calibration unit 48 is operated by a valve control subroutine which can be developed by one skilled in the art in accordance with the above description of the operation of the calibration unit 48.

Step 1110: Determine if the monitored chemical characteristics during calibration are within expected values, i.e., are the monitored chemical characteristics in the range of the predetermined chemical characteristics of the conditioned influent fluid sample stream.

Step 1112: If it is determined, at step 1110, that the chemical characteristic monitored by a particular instrument is not within the range of expected values during calibration, the operator is alerted of the malfunction of the particular instrument. The processing then proceeds to flow J (FIG. 15).

Step 1114: If the responses during calibration are all within the expected values, the cation conductivity is recalculated using the new calibration factors.

Step 1116: Determine if the monitored and calculated cation conductivities are approximately equal. If the conductivities are approximately equal, processing proceeds to flow J.

Step 1118: If the measured and calculated cation conductivities do not match, the operator is alerted of the presence of an unmeasured anion and processing continues to flow J.

It will be apparent to one skilled in the art, from the detailed specification, that the number of fluid lines 10 and thus the number of continuous monitor modules 20 is not limited; the steam cycle water from only one point in a power plant steam cycle or the steam cycle water from n points in a power plant steam cycle may be monitored by using 1 to n fluid lines 10 and continuous monitor modules 20. Additionally, each continuous monitor module 20 may serve to analyze influent fluid sample streams derived from one or more points in the power plant steam cycle by one or more fluid lines 10. Further, although it may be advantageous to employ plural cation conductivity monitors 32 for receiving a portion of each influent fluid sample stream and monitoring the cation conductivity thereof, a single cation conductivity monitor 32 could be shared by a plurality of continuous monitor modules 20 since altered third fluid sample streams having cations, including ammonia, removed therefore, are only required when the corresponding fluid sample stream is being supplied to the ion chromatograph unit 42. The use of a single ion chromatograph unit 42 likewise is not limiting in that the system could be expanded to operate with more than one ion chromatograph unit 42 — groups of influent fluid sample streams could be supplied to each of several ion chromatograph units, or an ion chromatograph unit could be provided for each influent fluid sample stream.

The many features and advantages of the automatic continuous on-line monitoring system of the present invention will be apparent to those skilled in the art from the detailed specification. Further, since numerous modifications and changes will readily occur to those skilled in the art, the claims are intended to cover all suitable modifications and equivalents falling within the true spirit and scope of the invention.

What is claimed is:

1. A system for automatic, continuous online monitoring of power plant steam cycle water at any of a plurality of different points in the power plant steam cycle, comprising:
   means for supplying, from at least a selected one of the plurality of points in the power plant steam cycle, a corresponding, selected influent fluid sample stream;
   for each selected influent fluid sample stream, a respectively associated continuous monitor module comprising:
   means for monitoring the temperature of the influent fluid sample stream and generating a corresponding temperature signal,
   means for continuously monitoring at least one selected chemical characteristic of the influent fluid sample stream from a first flow path and a second flow path and, in response thereto, generating a corresponding continuous monitor signal, and
   calibration means, including conditioning means for creating a pressure differential in the influent fluid sample stream from the second flow path and for utilizing the pressure differential to inject a mixed standard solution into the influent fluid sample stream to provide a conditioned influent fluid sample stream having predetermined chemical characteristics, and means selectively operable to establish the first and second fluid sample stream flow paths responsive to calibration actuation signals, the first flow path providing at least a portion of the influent fluid sample stream to said continuously monitoring means, and the second flow path providing the influent fluid sample steam to said conditioning means and at least a portion of the conditioned influent fluid sample stream to said continuously monitoring means;
   means for receiving a fractional portion of each selected influent fluid sample stream and monitoring the cation conductivity thereof, and, in response thereto, generating a corresponding cation conductivity signal and providing a corresponding altered fluid sample stream from which cations have been removed;
   ion chromatograph means for monitoring at least one chemical characteristic of each selected influent fluid sample stream and at least one selected chemical characteristic of the corresponding altered fluid sample stream responsive to a chromatograph actuation signal, and, in response to said chromatograph actuation signal, generating corresponding first and second chromatograph signals; and
   control means, responsive to at least the temperature signal, the cation conductivity signal and the first and second chromatograph signals corresponding to each selected influent fluid sample stream, for calculating the cation conductivity of the respective, selected influent fluid sample stream using predetermined conductivity equations, comparing the calculated cation conductivity with the monitored cation conductivity for the respective influent fluid sample stream, and generating said calibration actuation signals and said chromatograph actuation signal responsive to said comparison, for supply to said respective continuous monitor module and said ion chromatograph means.

2. An automatic, continuous on-line monitoring system according to claim 1, said calibration means further comprising means for deionizing the influent fluid sample stream to provide a deionized influent fluid sample stream; wherein the second flow path provides the influent fluid sample stream to said deionizing means, the deionized influent fluid sample stream to said conditioning means, and a conditioned, deionized influent fluid sample stream to said continuously monitoring means.

3. An automatic, continuous on-line monitoring system according to claim 2, said calibration means further comprising a drain; said selectively operable means being selectively operable to establish a third fluid sample stream flow, the third flow path providing the influent fluid sample stream to said deionizing means, the deionized influent fluid sample stream to said conditioning means, and the conditioned, deionized influent fluid sample steam to said drain.

4. An automatic, continuous on-line monitoring system according to claim 3, wherein said deionizer means and said conditioning means each have an input and an output;

said selectively operable means comprising:
a flow-splitter having an input for receiving the influent fluid sample stream and first and second outputs for supplying first and second portions of the influent fluid sample stream, respectively,
an on-off valve having an input and an output, and being selectively operable between open and closed positions,
a two-way valve having an input, a first output, and a second output in fluid communication with said drain producing a fourth flow path, and being selectively operable between first and second positions, the first position connecting said input and said first output thereof and the second position connecting said input and said second output thereof,
a first parallel fluid line interconnecting said first output of said flow-splitter and said input of said on-off valve,
a second parallel fluid line having first, second and third portions, said portion interconnecting said second output of said flow-splitter and said input of said deionizing means, said second portion interconnecting said output of said deionizing means and said input of said conditioning means, and said third portion interconnecting said output of said conditioning means and said input of said two-way valve, and
an output fluid line interconnecting said output of said on-off valve and said first output of said two-way valve with said continuously monitoring means;
said on-off valve, in the open position thereof, interconnecting said first parallel fluid line and said output fluid line and establishing therewit said first fluid sample stream flow path for providing at least a further portion of said first portion of the influent fluid sample stream to said continuously monitoring means;
said two-way valve, in the first position thereof, interconnecting said third portion of said second parallel fluid line with said output fluid line and establishing therewith, and with said deionizing means, said conditioning means, and said first and second portions of said second parallel fluid line, said second fluid sample stream flow path for providing said second portion of the influent fluid sample stream to said deionizing means, said deionized influent fluid sample steam to said conditioning means, and at least a further portion of said conditioned, deionized second fluid sample stream to said continuously monitoring means; and
said two-way valve, in the second position thereof, interconnecting said third portion of said second parallel fluid line with said drain and establishing therewith, and with said deionizing means, said conditioning means, and said first and second portions of said second parallel fluid line, said third fluid sample stream flow path for providing said second influent fluid sample stream to said deionizing means, said deionized said influent fluid sample stream to said conditioning means and said conditioned, deionized second fluid sample stream to said drain.

5. An automatic, continuous on-line monitoring system according to claim 2, wherein said control means calibrates the continuous monitor signal, the cation conductivity signal, and the first and second chromatograph signals in dependence on the predetermined chemical characteristics of the conditioned influent fluid sample stream.

6. An automatic, continuous-on-line monitoring system according to claim 1, wherein said mixed standard solution comprises chemicals selected from the group of $NH_4OH$, $NaCl$, $SO_4$, $Cu$, $Fe$, and $F$.

7. An automatic, continuous on-line monitoring system according to claim 1, wherein said mixed standard solution comprises organic acids.

8. A system for automatic, continuous online monitoring of steam cycle water in a nuclear reactor, said system comprising:
plural supply means for supplying, from a plurality of different points in the power plant steam cycle, correspondng influent fluid sample streams;
a plurality of continous monitor module means, corresponding to respective ones of said influent fluid sample streams, each continuous monitor module comprising:
means for monitoring the temperature of said influent fluid sample stream and generating a temperature signal representative of the monitored temperature,
calibration means, including conditioning means for creating a pressure differential in the influent fluid sample stream and for utilizing the pressure differential to inject to mixed standard solution into the influent fluid sample stream to provide a conditioned influent fluid sample stream having predetermined chemical characteristics, first flow-splitter means for dividing said influent fluid sample steam into first and second influent fluid sample streams, and means selectively operable to establish first and second fluid sample stream flow paths responsive to calibration actuation signals, the first flow path providing the influent fluid sample stream to said first flow-splitter means, and the second flow path providing the influent fluid sample stream to said conditioning means and the conditioned influent fluid sample stream to said first flow splitter means, and
means for continuously monitoring at least one selected chemical characteristic of said first influent fluid sample stream and, in response thereto generating a corresponding continuous monitor signal;
a plurality of second flow-splitter means for dividing each of said second influent fluid sample streams into third and fourth influent fluid sample streams;
means for receiving each third influent fluid sample stream and monitoring the cation conductivity thereof, and, in response thereto, generating a corresponding cation conductivity signal and providing a corresponding, altered third fluid sample stream from which cations have been removed;

ion chromatograph means for for monitoring at least one selected chemical characteristic of each of said altered third fluid sample streams responsive to chromatograph actuation signals and for monitoring at least one chemical characteristic of the corresponding fourth influent fluid sample stream and for generating chromatograph signals representative of the monitored selected chemical characteristics;

means selectively operable to supply said plural altered third fluid sample streams and corresponding fourth influent fluid sample streams to said ion chromatograph means in individual succession in a sampling sequence; and control means, responsive to at least the temperature, continuous monitor, cation conductivity and chromatograph signals corresponding to each influent fluid sample stream, for:

determining said sampling sequence, calculating the cation conductivity for the influent fluid sample stream corresponding to the altered third and fourth influent fluid sample streams being supplied to said ion chromatograph means using predetermined conductivity equations, comparing said calculated cation conductivity with the monitored cation conductivity of the corresponding influent fluid sample stream to select the chemical characteristics to be monitored by said ion chromatograph means and to determine if calibration is necessary, selectively generating said calibration actuation signals at predetermined time intervals, and generating said chromatograph actuation signal in dependence on said chemical characteristic selected by comparing said calculated cation conductivity with said monitored cation conductivity.

9. An automatic, continuous on-line monitoring system according to claim 8, said calibration means further comprising means for deionizing the influent fluid sample stream to provide a deionized influent sample stream; wherein the second flow path provides the influent fluid sample stream to said deionizing means, the deionized influent fluid sample stream to said conditioning means, and a conditioned, deionized influent fluid sample stream to said first flowsplitter means.

10. An automatic, continuous on-line monitoring system according to claim 9, said calibration means further comprising a drain; said selectively operable means being selectively operable to establish a third fluid sample stream flow path, the third flow path providing the influent fluid sample stream to said deionizing means, the deionized influent fluid sample stream to said conditioning means, and the conditioned, deionized influent fluid sample stream to said drain.

11. An automatic, continuous on-line monitoring system according to claim 8, wherein said mixed standard solution comprises chemicals selected from the group of $NH_4OH$, $NaCl$, $SO_4$, $Cu$, $Fe$, $F$, formic acid and acetic acid.

12. A system for on-line calibration of at least one chemical monitor, the at least one monitor including a detector for sensing the level of a selected chemical characteristic of an influent fluid sample stream and producing an output representative of the sensed level of the selected chemical charcteristic, said system for on-line calibration comprising:

conditioning means for creating a pressure differential in the influent fluid sample stream and for utilizing the pressure differential to inject a standard solution into the influent fluid sample stream to provide a conditioned fluid sample stream having a predetermined level of each selected chemical characteristic;

means; coupled to said conditioning means and said detectors, for selectively establishing first and second fluid sample stream flow path, the first flow path providing the influent fluid sample stream to the detector, and the second flow path providing the influent fluid sample stream to the conditioning means and the conditioned fluid sample stream to the detector; and means for calibrating each output representative of the sensed level of the corresponding, selected chemical characteristic with respect to the predetermined level of the selected chemical characteristic in the conditioned fluid sample stream.

* * * * *